US012648870B2

(12) United States Patent     (10) Patent No.: US 12,648,870 B2

Alfonso et al.     (45) Date of Patent:    Jun. 9, 2026

(54) TRACTION TOWER TRAP AND FINGER TRAP SYSTEM

(71) Applicant: Conmed Corporation, Utica, NY (US)

(72) Inventors: Gregory Alfonso, Seffner, FL (US);
Robert Thibodeau, Saint Petersburg,
FL (US); Matthew C. Summitt, Palm
Harbor, FL (US); Thien Vu, Pinellas
Park, FL (US); Jennifer Hicks, Cocoa,
FL (US); Brenda Yantzer, Temple
Terrace, FL (US)

(73) Assignee: Conmed Corporation, Utica, NY (US)

( * ) Notice: Subject to any disclaimer, the term of this
patent is extended or adjusted under 35
U.S.C. 154(b) by 489 days.

(21) Appl. No.: 17/622,420

(22) PCT Filed: Jun. 5, 2020

(86) PCT No.: PCT/US2020/036376

§ 371 (c)(1),
(2) Date: Dec. 23, 2021

(87) PCT Pub. No.: WO2021/006971

PCT Pub. Date: Jan. 14, 2021

(65) Prior Publication Data

US 2022/0354683 A1     Nov. 10, 2022

Related U.S. Application Data

(60) Provisional application No. 62/930,115, filed on Nov.
4, 2019, provisional application No. 62/871,146, filed
on Jul. 7, 2019.

(51) Int. Cl.
| | |
|---|---|
| *A61F 5/04* | (2006.01) |
| *A61G 13/12* | (2006.01) |
| *A61H 1/02* | (2006.01) |

(52) U.S. Cl.
CPC .............. *A61F 5/04* (2013.01); *A61G 13/124*
(2013.01); *A61H 1/0274* (2013.01)

(58) Field of Classification Search
CPC ...... A61H 1/02; A61H 1/0218; A61H 1/0222;
A61H 1/0229; A61H 1/0237; A61H
1/024;
(Continued)

(56) References Cited

U.S. PATENT DOCUMENTS 3,850,166 A * 11/1974 Tamny ...................... A61F 5/04
602/40
3,872,861 A     3/1975 Tamny et al.
(Continued)

FOREIGN PATENT DOCUMENTS

| CN | 203915158 U | 11/2014 |
|---|---|---|
| CN | 205286591 U | 6/2016 |

(Continued)

OTHER PUBLICATIONS

International Search Report Form PCT/ISA/220, International Appli-
cation No. PCT/US2020/036376 pp. 1-19, Dated Sep. 7, 2020.
(Continued)

*Primary Examiner* — Adam Baker
(74) *Attorney, Agent, or Firm* — Frederick J.M. Price;
Bond, Schoeneck & King, PLLC

(57) ABSTRACT

A traction tower trap assembly with straps and finger traps
that are easily adjustable and releasable. The traction tower
assembly includes straps for parts of the arm, such as the
patient's bicep or forearm, and finger traps to traction parts
of the arm and fingers for surgical procedures. The forearm
traction tower assembly includes a tower having first and
second sides. The tower is connected to a base plate with a
first and second slots extending partially therethrough. The
assembly includes a strap made of a length of material (Continued)

attached to first and second adjustment mechanisms. The first adjustment mechanism is slidable within the first slot of the base plate and the second adjustment mechanism is slidable within the second slot of the base plate.

6 Claims, 45 Drawing Sheets

(58) Field of Classification Search
CPC .. A61H 1/0244; A61H 1/0266; A61H 1/0274; A61H 1/0277; A61H 1/0281; A61H 1/0285; A61H 1/0288; A61F 5/04; A61F 5/042; A61F 5/05; A61F 5/05833; A61F 5/0585; A61F 5/05858; A61F 5/05866; A61F 5/10; A61F 5/37; A61F 5/3761; A61F 5/3723; A61G 13/0045; A61G 13/124; A61G 13/1235; A61G 1/00; A61G 1/044
USPC .......................................................... 602/32
See application file for complete search history.

(56) References Cited

U.S. PATENT DOCUMENTS

| | | | | |
|---|---|---|---|---|
| 4,005,506 | A | | 2/1977 | Moore |
| 4,445,506 | A | | 5/1984 | Johansson et al. |
| 4,655,206 | A | * | 4/1987 | Moody .................... A61G 1/04 |
| | | | | 5/628 |
| 5,074,291 | A | | 12/1991 | Carter |
| 5,113,876 | A | * | 5/1992 | Herman ................. A61G 1/044 |
| | | | | 5/628 |
| 5,451,203 | A | | 9/1995 | Lamb |
| 5,632,726 | A | | 5/1997 | Repice et al. |
| 5,702,355 | A | | 12/1997 | Repice |
| 5,868,691 | A | | 2/1999 | Vishnevsky |
| 6,092,525 | A | * | 7/2000 | Church .................... A61G 1/01 |
| | | | | 128/869 |
| 6,517,506 | B1 | * | 2/2003 | Pettibon .................... A61F 5/04 |
| | | | | 602/32 |
| 6,533,741 | B1 | | 3/2003 | Lee et al. |
| 2002/0002977 | A1 | * | 1/2002 | Tyrrell ..................... A61G 1/01 |
| | | | | 128/869 |
| 2004/0133140 | A1 | | 7/2004 | Aduana et al. |
| 2005/0240136 | A1 | * | 10/2005 | Price ......................... A61F 5/04 |
| | | | | 602/32 |
| 2006/0161086 | A1 | | 7/2006 | Lambert |
| 2007/0135748 | A1 | | 6/2007 | Price |
| 2010/0234776 | A1 | | 9/2010 | Borden |
| 2012/0103344 | A1 | | 5/2012 | Hunter, Jr. |
| 2019/0116924 | A1 | * | 4/2019 | Darby .................... A43B 13/36 |

FOREIGN PATENT DOCUMENTS

| | | |
|---|---|---|
| CN | 105997163 A | 10/2016 |
| CN | 107028628 A | 8/2017 |
| CN | 108309672 A | 7/2018 |
| CN | 208130227 U | 11/2018 |
| GB | 1457180 A | 12/1976 |
| JP | 2012040228 A | 3/2012 |
| WO | 2011112658 A1 | 9/2011 |

OTHER PUBLICATIONS

AU Examination Report No. 2, Application No. 2023202345, dated Nov. 4, 2024, entire document.
"CN Office Action, Application No. 202080049298.9, dated May 30, 2024, entire document".
CN Office Action 2, Application No. 202080049298.9 , dated Nov. 27, 2024, entire document.
EP Search Report; Application No. 25152461.7; dated May 12, 2025, Entire document.
EP Search Report; Application No. 25152464.1; dated May 12, 2025, Entire document.
P Office Action, Application No. 2024-191396, dated Dec. 16, 2025, entire document.

* cited by examiner

TRACTION TOWER TRAP AND FINGER TRAP SYSTEM

CROSS-REFERENCES TO RELATED APPLICATIONS

This application is a national stage application under 35 U.S.C. 371 based on international patent application PCT/US20/36376 filed on Jun. 5, 2020, which claims priority to U.S. Provisional Patent Application Ser. No. 62/871,146, filed on Jul. 7, 2019 and entitled "Traction Tower Trap and Finger Trap System," and U.S. Provisional Patent Application No. 62/930,115, filed on Nov. 4, 2019 and entitled "Traction Tower Scale," and is related to PCT Application PCT/US20/16170, filed on Jan. 31, 2020 and entitled "Wrist Traction Tower," the entireties of which are incorporated herein by reference.

BACKGROUND OF THE INVENTION

1. Field of the Invention

The present invention relates to orthopedic medical procedure positioning devices/systems and, more particularly, to a wrist traction tower trap and finger trap system.

2. Description of Related Art

During arthroscopic surgery in the wrist, for example, surgeons use traction to create enough space in the wrist joint for the appropriate and efficient use of an arthroscope and other related instruments. Conventional traction towers are commonly used to create such traction needed for wrist arthroscopic surgical procedures, radiographic procedures and other related medical procedures. Strap and finger traps are used with the traction tower to assist in positioning and distracting the patient's arms for orthopedic hand and wrist surgical procedures. The straps provide an atraumatic method for securing the patient's forearm and bicep to the traction tower. The finger traps retain an atraumatic method of securing the patient's fingers. However, conventional traction tower straps and finger traps are limited in their ability to accommodate a wide variety of individual patient sizes and difficult to tighten and release from each patient.

Therefore, there is a need for traction tower straps and finger traps that are easily adjustable and releasable.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a wrist traction tower and related traction tower scale.

Embodiments of the wrist traction tower are directed to a system with multiple parts, one or more of which are configured, attached, positioned and/or structured to move (e.g., slide, telescope, rotate, twist, turn) with respect to one or more of the other parts of the system. Such adjustability, maneuverability and flexibility provide for an improved and enhanced orthopedic medical procedure positioning system (as compared to conventional devices/systems), which can accommodate a wide variety of lengths and sizes of patients' arms while at the same time providing sufficient space for medical practitioners and their respective equipment to perform surgical, radiographic and other related medical procedures. Elements of the traction tower system of an embodiment can be made of Aluminum, Stainless Steel, Brass, and Plastic (PEEK).

According to one aspect, the present invention is a traction tower assembly. The traction tower assembly can include a first tower having a first side surface and a second tower having a second side surface positioned adjacent to the first side surface, wherein the second tower is movable with respect to the first tower in a first direction and in a second direction; and an elongated arm assembly attached to and extending from the tower assembly. A traction tower scale can also be part of an embodiment of the present invention.

Embodiments of the present invention take into consideration that, in one preferred embodiment, when positioning the height of upper tower and connected arm assembly with respect to the lower tower, an individual patient's wrist joint should be about 1 inch above the rotation joint (as identified below). This allows a medical practitioner to, for example, x-ray the wrist while keeping it attached to the traction tower. If there is metal too close to the wrist joint, the x-ray image could be affected.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
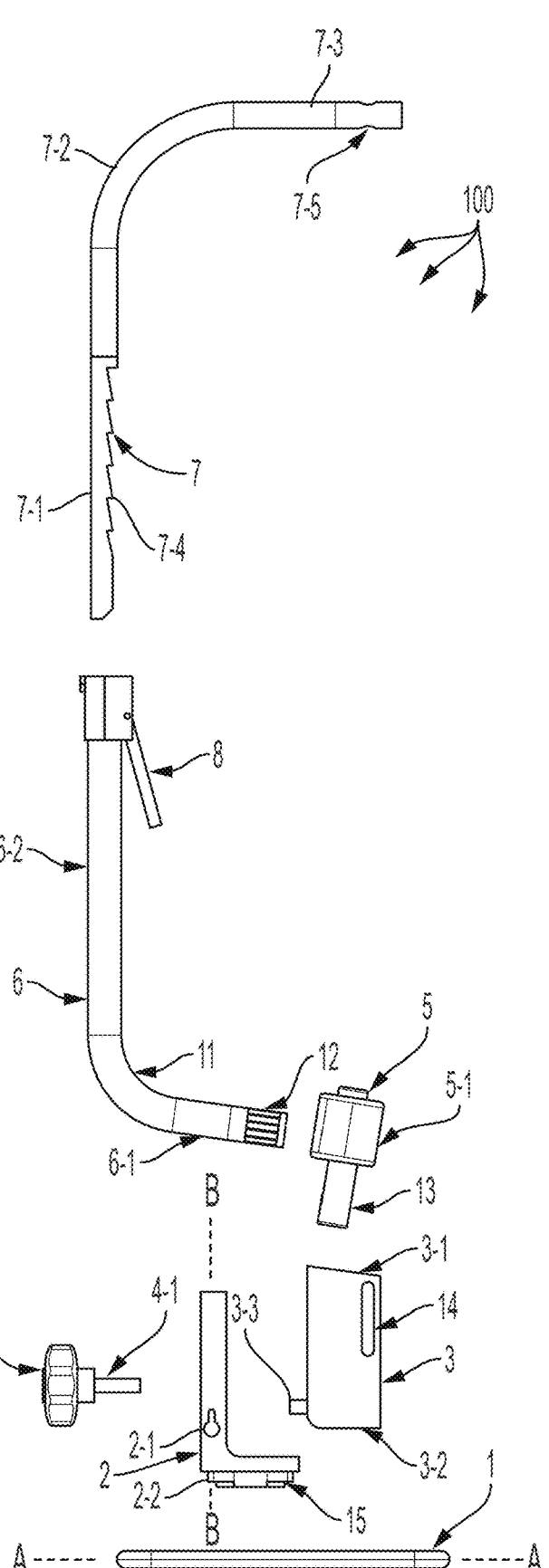
FIG. 1 is an exploded perspective view schematic representation of a traction tower, according to an embodiment.
Figure 2:
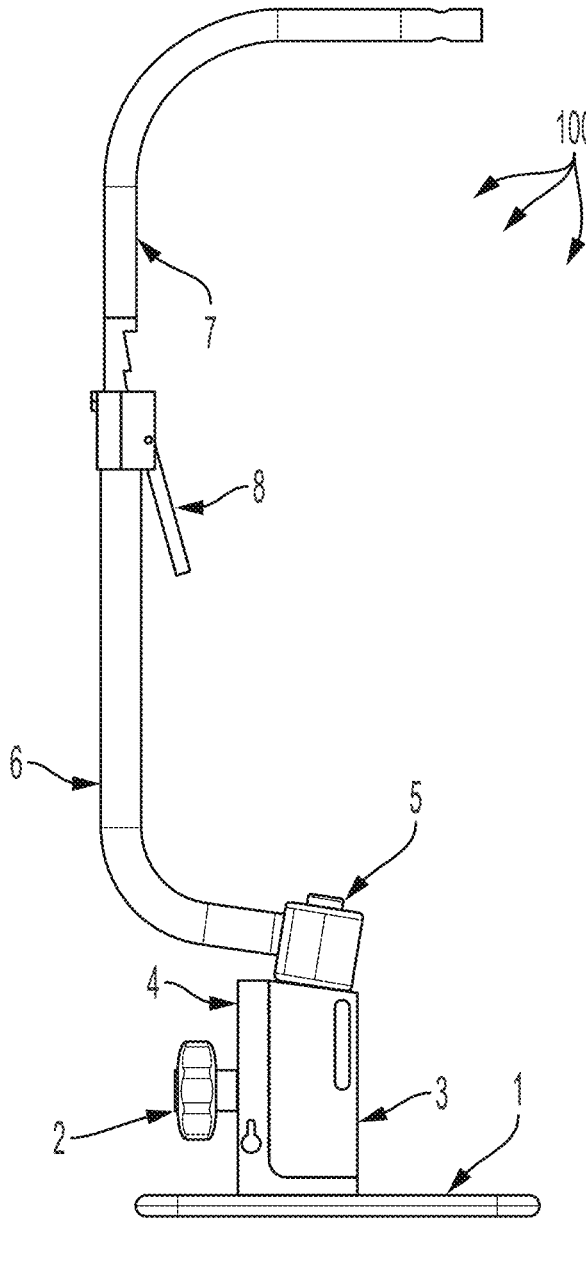
FIG. 2 is an assembled perspective view schematic representation of the traction tower shown in FIG. 1, according to an embodiment.
Figure 3:
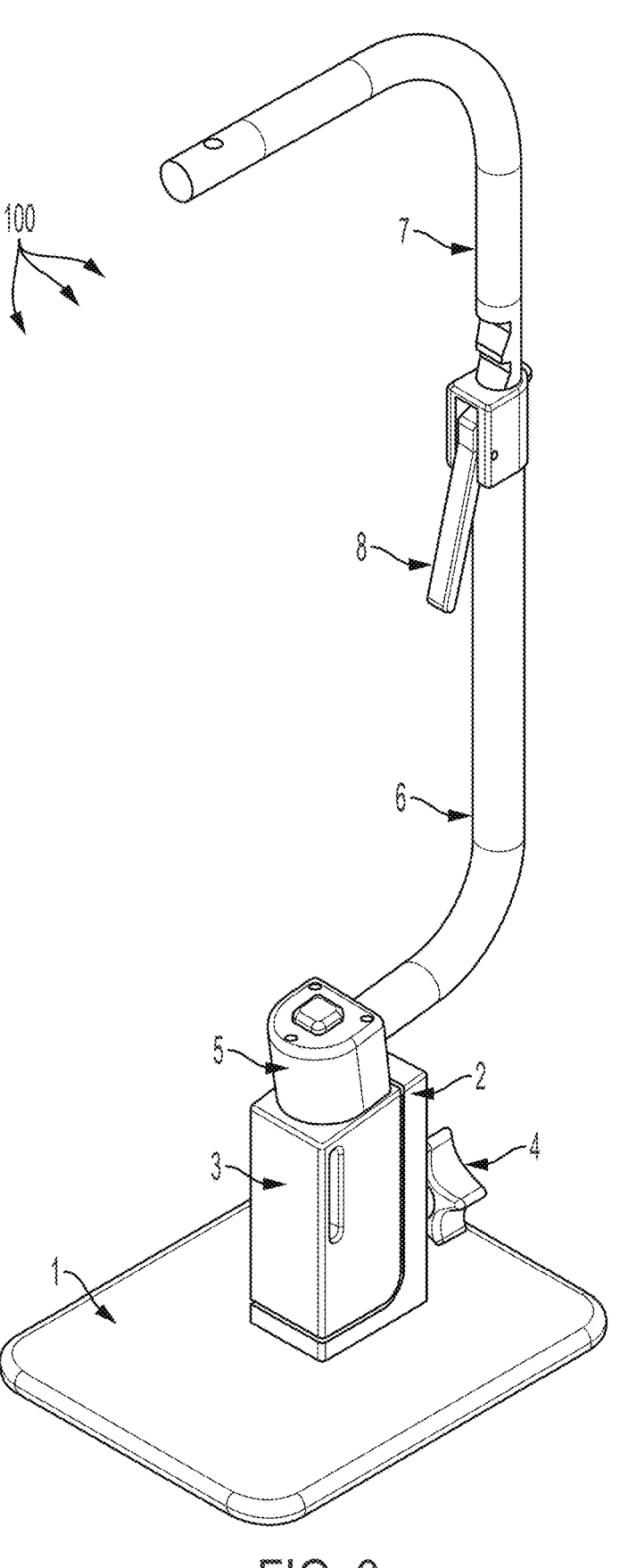
FIG. 3 is an assembled perspective view schematic representation of the traction tower shown in FIG. 1, according to an embodiment.

Referring now to the figures, wherein like reference numerals refer to like parts throughout, FIG. 1 shows an exploded perspective view schematic representation of a traction tower 100 according to an embodiment. FIGS. 2 and 3 are assembled perspective view schematic representations of the traction tower 100 shown in FIG. 1, according to an embodiment. As shown, the traction tower 100 includes a base plate 1, a tower assembly, and an arm assembly. The tower assembly is shown having multiple parts—a lower tower 2 and an upper tower 3—that fit together, and where the upper tower 3 is moveable with respect to the lower tower 2 (as discussed further below). The lower tower 2 is removably securable on the base plate 1 (via any attachment means 15 including a clip, keyed slide and lock mechanism, nut and bolt etc., as should be understood by a person of ordinary skill in the art in conjunction with this disclosure). In addition, the lower tower 2 can include a peg 2-2, which is biased in the downward (protruding from the bottom surface of the lower tower 2) direction via a spring (not shown) positioned in the lower tower 2. The peg 2-2 can be lifted up by sliding button 2-1, and be fully positioned within the lower tower 2. The peg 2-2 can fit into a hole formed in the base plate 1 (not shown), and the lower tower can then be turned (clockwise or counterclockwise) to assist with the locking of the lower tower 2 to the base plate 1. According to an embodiment, all other elements/parts of the traction tower 100 can be, but do not have to be, moveable with respect to at least one other element/part of the traction tower 100.

Still referring to FIGS. 1-3, lower tower 2 is L-shaped and is configured to snuggly fit upper tower 3 as shown. The tower assembly can include additional pieces, and can include multiple shapes as long as the pieces fit together in a snug arrangement and the overall movement and locking functionality is similar or remains the same as described herein. The tower assembly components (here the lower tower 2 and upper tower 3), can be secured/locked together by a locking knob 4. The stem 4-1 of locking knob 4 is positionable through lateral apertures positioned in each of lower tower 2 and upper tower 3, and the knob end can be turned to secure each tower component together (as should be understood by a person of skill in the art in conjunction with a review of this disclosure). The aperture in the upper tower 3 is a hole (not shown) shaped to snugly fit, engage and secure the stem of the locking knob 4 when the knob end is turned in the appropriate direction (and be disengaged and be released from the aperture in the upper tower when the knob is turned in the opposite direction). The aperture 2-3 in lower tower 2 is elongated up and down (partially shown in FIG. 9) to allow for upward and downward movement of the upper tower 3 with respect to the lower tower 2, where the upper tower 3 can be resecured to the lower tower 2 per use of the locking knob 4 (as described herein and as should be understood by a person of ordinary skill in the art in conjunction with a review of this disclosure). In accordance with an additional embodiment, the lower tower 2 can include a different or additional elongated aperture(s) to allow for relative movement of the upper tower 3 with respect to the lower tower 2 in a diagonal direction, horizontal direction, or other directions at an angle to the vertical direction B - - - B when assembled. In accordance with an alternative embodiment, the types of apertures could be reversed between the upper 3 and lower 2 towers. Upper tower 3 also can include an aperture or through hole 14 (longitudinally shaped or other shapes) that can accommodate a strap to hold a patient's forearm to the traction tower 100. The upper tower 3 also includes an alignment peg 3-3, which is configured to fit into a corresponding elongated hole (up and down, not shown) in the lower tower 2. This alignment peg 3-3 acts in conjunction with the stem 4-1 to assist with the alignment of the upper tower 3 with respect to the lower tower 2 and to prevent the upper tower 3 from unwanted movement/rotation with respect to the lower tower 2 when the relative height of the upper tower 3 is adjusted with respect to the lower tower 2.

Continuing to refer to FIGS. 1-3, a rotation joint 5 connects the tower assembly to the arm assembly. A stem 13 of the rotation joint 5 is positionable and rotatable in the upper tower 3 (as shown, positioned through the top surface 3-1 of the upper tower 3, and as discussed further below). The top surface 3-1 of the upper tower is configured to extend along a plane at an angle to the bottom surface 3-2 and/or to the plane of the base plate 1 A - - - A when assembled. Alternatively, the top surface 3-1 can extend along a plane that is parallel to the plane of the base plate 1 A - - - A. The first end of the lower arm 6 includes a slotted base end 12, which is removably positionable, rotatable and lockable within the head 5-1 of the rotation joint 5 (as discussed further below). Lower arm 6 extends away from the slotted base end 12 and an elongated lower end 6-1 to a curved portion 11 of the lower arm 6, which extends to an elongated upper end 6-2 of the lower arm 6. Upper end 6-2 of the lower arm 6 extends at an angle to an axis (which can be any angle including 45 degrees, substantially perpendicular to perpendicular) of the elongated lower end 6-1. An elongated lower end 7-1 of the upper arm 7, can but does not have to be solid, fits and is telescopically moveable within the elongated upper end 6-2 of the lower arm 6, which is formed as a tube. Lever 8 is connected to elongated upper end 6-2 of the lower arm 6. Lever 8 includes a protrusion or tooth on the end positioned within the elongated upper end 6-2 of the lower arm 6, which can be positioned and fit in between the ridges 7-4 formed on at least one side of the elongated lower end 7-1 of the upper arm 7 (which faces the protrusion or tooth of lever 8 when the elongated lower end 7-1 of the upper arm 7 is positioned within the elongated upper end 6-2 of the lower arm 6). When lever 8 is actuated in a first direction positioning the protrusion or tooth in between one of the pairs of ridges 7-4, the upper arm 7 is fixed/secured/locked with respect to the lower arm 6. When lever 8 is actuated in a second direction, the upper arm 7 is released from its fixed/secured/locked position and is free to move with respect to the lower arm 6 (e.g., further within or without the lower arm 6). In accordance with an alternative embodiment, upper arm 7 can be tubular in structure, and lower arm 6 can be solid/non-tubular (but does not have to be) and contain ridges (essentially the opposite configuration shown in FIG. 1). The lever arm 8 can be any type of actuator including a linear slider, circular actuator or switch etc. (as should be understood by a person of ordinary skill in the art in conjunction with a review of this disclosure).

Elongated lower end 7-1 of the upper arm 7 extends away from the lower arm to a curved portion 7-2 of the upper arm 7, which extends to an elongated upper end 7-3 of the upper arm 7. Upper end 7-3 of the upper arm 7 extends at an angle to an axis (which can be any angle including 45 degrees, substantially perpendicular to perpendicular) of the elongated lower end 7-1, and in essentially the same direction as the elongated lower end 6-1 of the lower arm 6 (and can extend, but does not have to, in a plane that is parallel or substantially parallel thereto; as shown, the elongated lower end 6-1 of the lower arm 6 points slightly more in the relatively downward direction as compared to elongated upper end 7-3 of the upper arm 7, which is shown extending in a plane that is parallel or substantially parallel to plane A - - - A). Elongated upper end 7-3 of the upper arm 7 includes a through hole 7-5 configured to assist with securing a traction tower scale (embodiments of the traction tower scale and its attachment to a traction tower are discussed further below) thereto.

As discussed above, there are several structural features and configurations that allow the traction tower 100 as a whole to be sized appropriately for an individual patient. In addition, as the height of the upper tower 3 is adjusted (as described with respect to FIGS. 4-5 below), the forearm strap position 14 will move with it and is always relatively close to the patient's wrist (the closer to the wrist the better control the strap has). If the strap was in one fixed position it wouldn't work great for different patient sizes.

Figure 4:
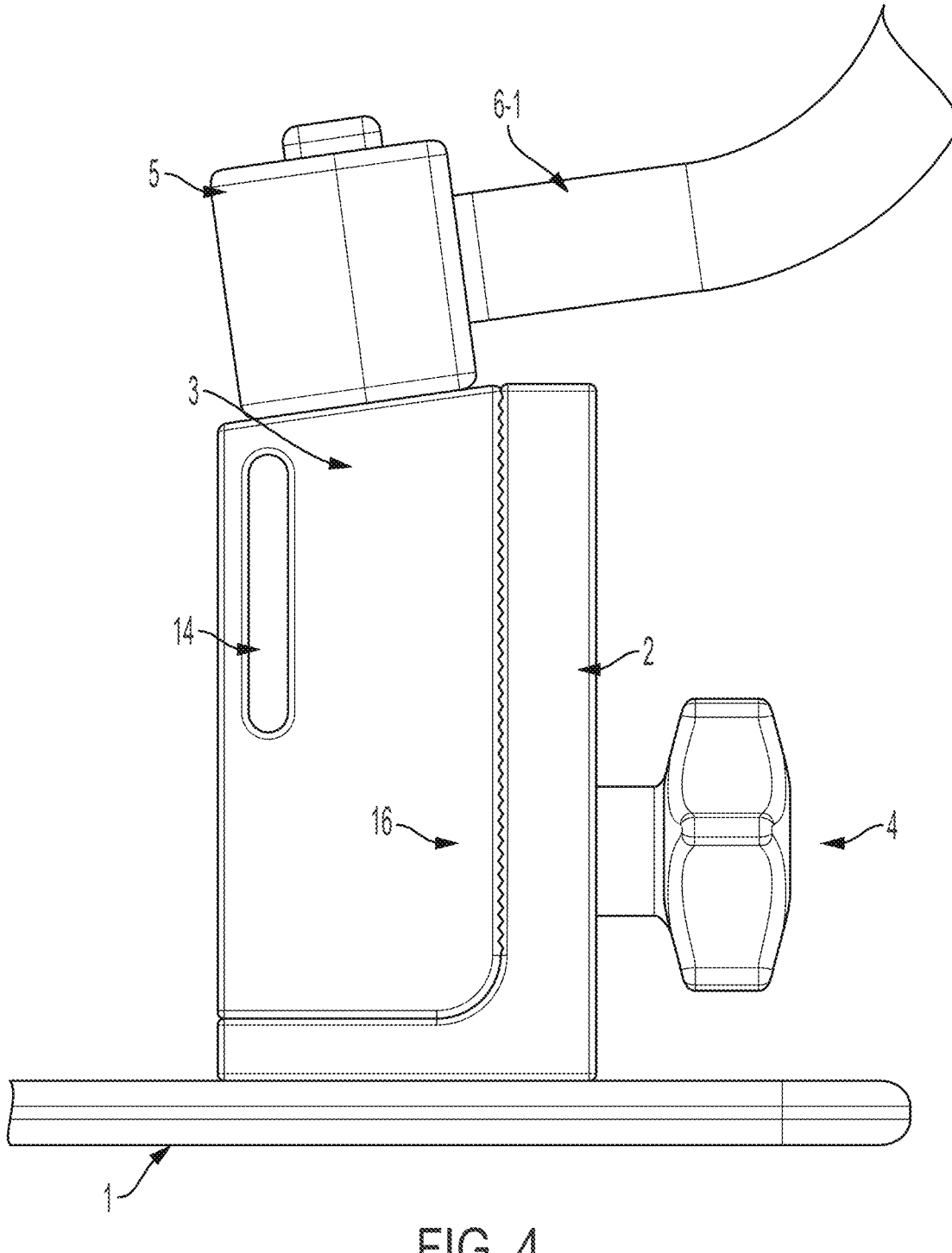
FIG. 4 is a close-up perspective view schematic representation of a lower portion of the traction tower shown in FIG. 1, according to an embodiment.
Figure 5:
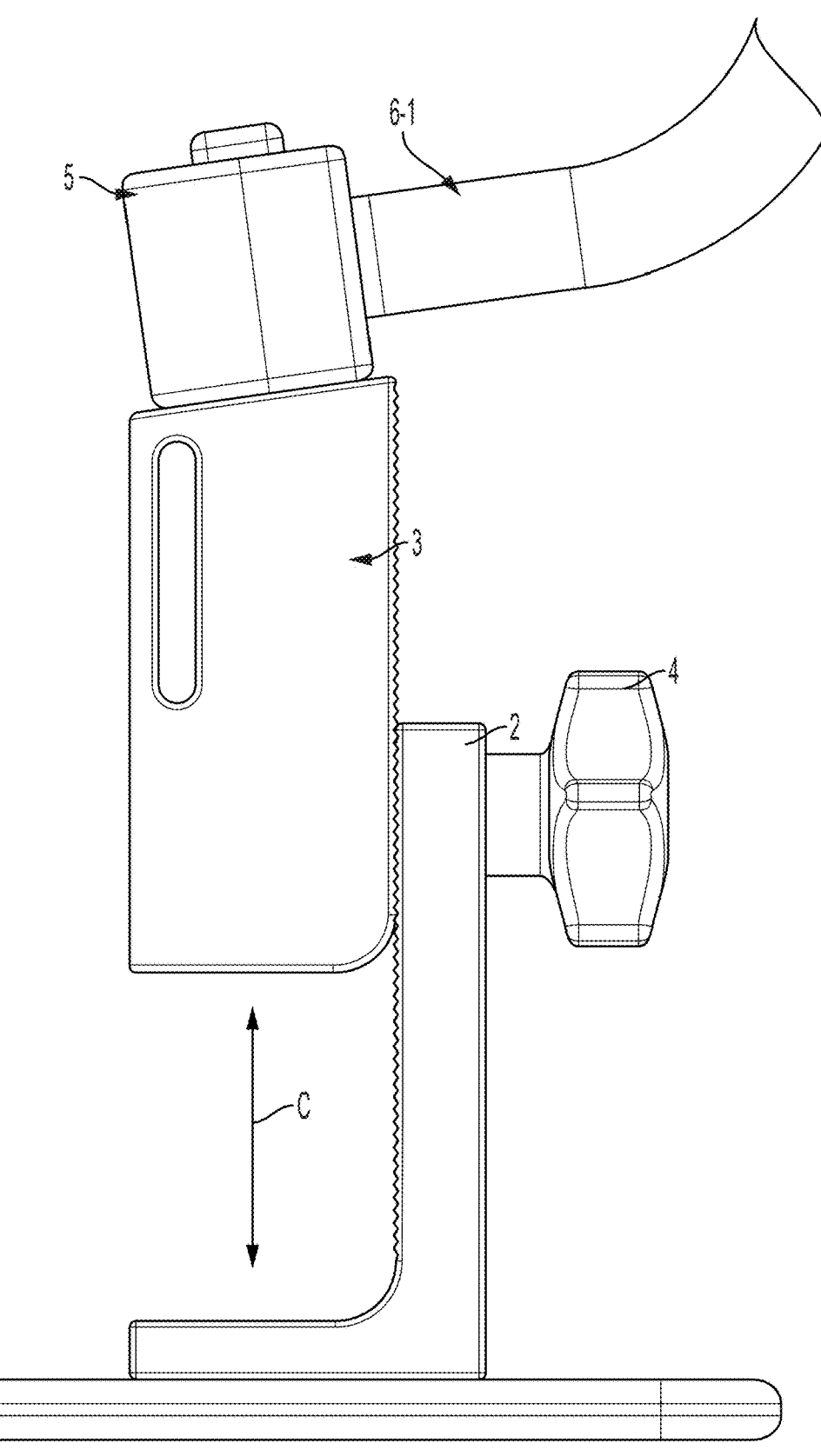
FIG. 5 is a close-up perspective view schematic representation of a lower portion of the traction tower shown in FIG. 1, according to an embodiment.

Turning to FIGS. 4-5, close up perspective view schematic representations of a lower portion of the traction tower 100 shown in FIG. 1 are provided, according to an embodiment. FIGS. 4-5 are provided to show movement of upper tower 3 with respect to lower tower 2 to accommodate a variety of individual patent forearm sizes, and the structural features that allow for such movement. FIG. 4 shows the upper tower 3 in its relatively lowest position with respect to lower tower 2, and FIG. 5 shows the upper tower 3 in its relatively highest position with respect to the lower tower 2.

Referring to FIG. 4, the upper tower 3 is shown fitting snugly within the outline of the lower tower 2 in the upper tower's 3 lowest position. As shown, the upper tower 3 and the lower tower 2 are held together by the locking knob 4 (as discussed above). An interlockable wave/serration pattern 16 may also be provided on each respective lateral facing surface of the upper tower 3 and lower tower 2 to assist with the locking of the upper tower 3 and the lower tower 2 together. The wave/serration pattern 16 can cover the whole of each respective lateral facing surface of the upper tower 3 and lower tower 2, or some portion less than the whole of each respective surface. Also, as discussed above, adjustment of the upper tower 3 upwards is accomplished by (1) loosening the locking knob 4 and connection between the upper tower 3 and lower tower 2, (2) movement of the knob 4 within the elongated aperture 2-1 (not shown) and upper tower 3 up from the position shown in FIG. 4 to the position shown in FIG. 5 and then tightening the locking knob 4 and upper tower 3 in the new position, and (3) as a result of the movement of the upper tower 3 in the up direction along arrow C, a number of other elements move in the up direction with respect to the lower tower 2 including the strap for the patient's arm (not shown) positionable through aperture 14, rotation joint 5, and the arm assembly. To move the upper tower 3 in the opposite direction, the same actions can be performed (i.e., starting with loosening of the locking knob 4, movement of the locking knob 4 and the upper tower 3 etc. in the opposite direction etc.).

As discussed above, the top surface 3-1 of the upper tower is configured to extend along a plane positioned at an angle to the plane of the base plate 1 A - - - A when assembled (see FIG. 1). The rotation joint 5, being attached to the top portion of the upper tower 3, includes a rotation axis A1 extending at an angle to a straight up and down vertical axis—see B - - - B of FIG. 1. By having the rotation joint 5, which houses a portion of the lower arm 6, positioned at an angle with an angled rotation axis A1 (see, e.g., FIG. 6, which shows the rotation axis A1 created by angling the rotation joint 5 positioned on and its stem 13 positioned within upper tower 3), the rotation of the rotation joint 5 and the arm assembly (explained further below) will not displace the point that the traction is created (as should be understood by a person of ordinary skill in the art in conjunction with a review of this disclosure). This means that the arm assembly can be moved as shown in FIGS. 7-8 without losing traction in the patient's arm or its position.

Figure 6:
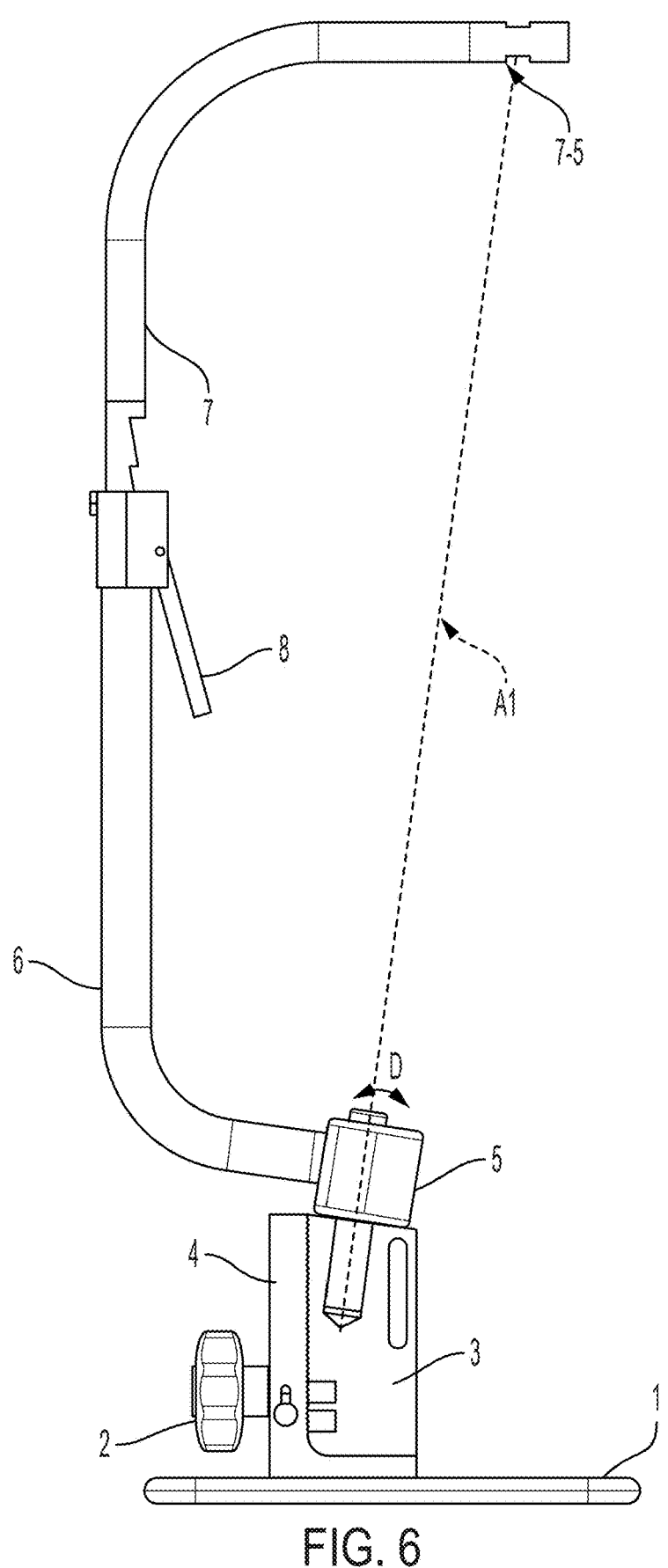
FIG. 6 is an assembled perspective view schematic representation of the traction tower shown in FIG. 1, according to an embodiment.
Figure 7:
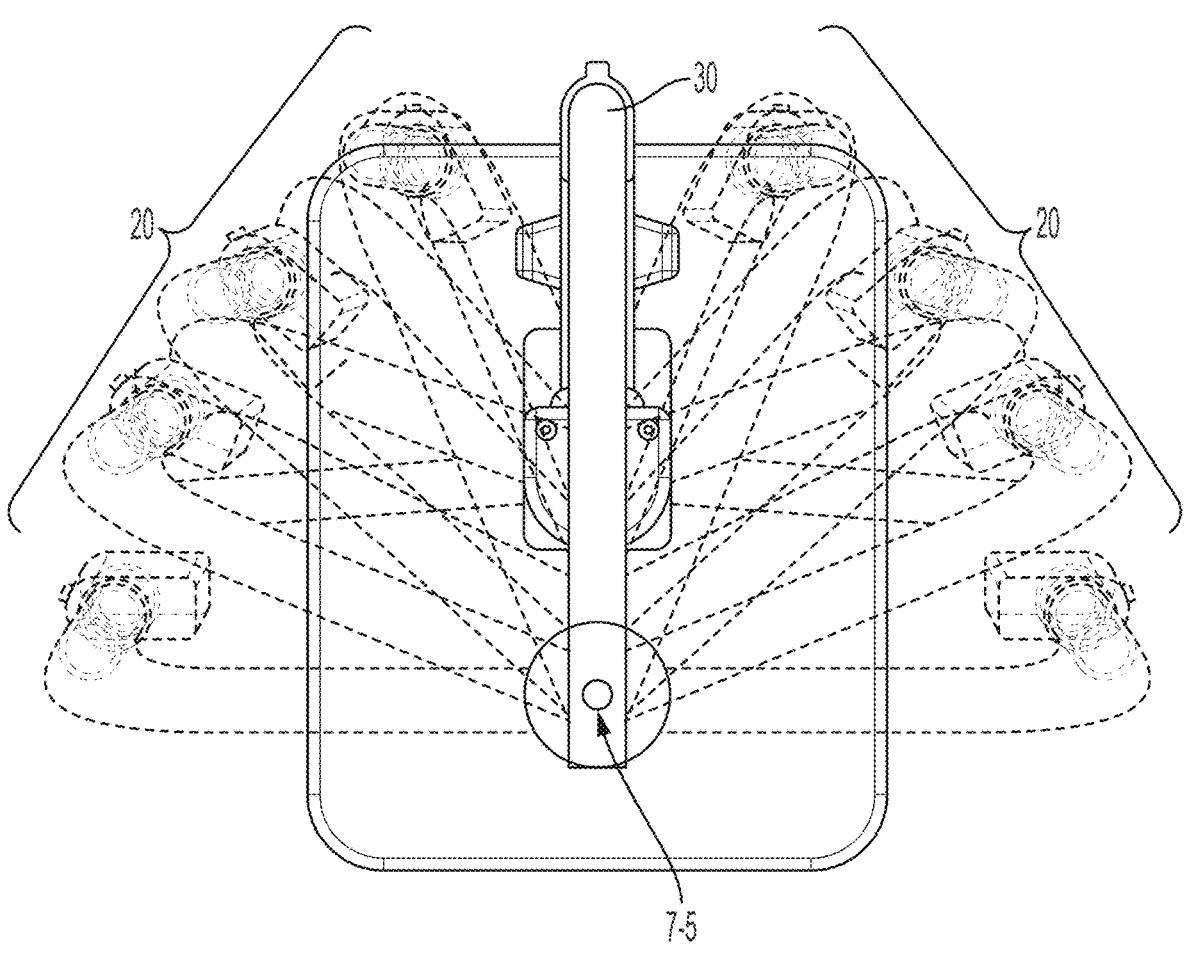
FIG. 7 is a top view schematic representation of the traction tower shown in FIG. 1, according to an embodiment.
Figure 8:
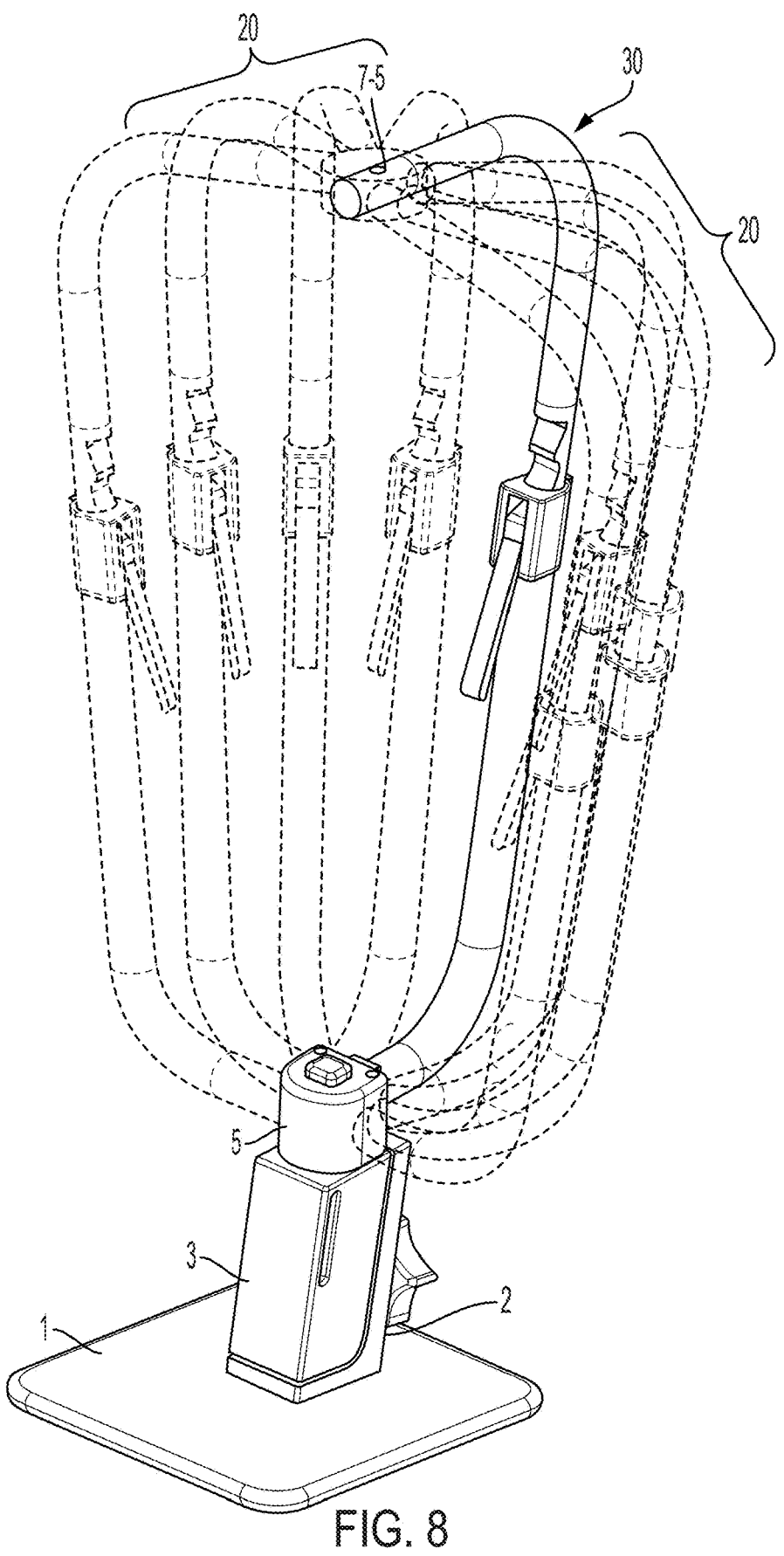
FIG. 8 is a perspective view schematic representation of the traction tower shown in FIG. 1, according to an embodiment.

Turning to FIGS. 7 and 8, top and perspective view schematic representations showing the rotation range of rotation joint 5 (and, thus, the arm assembly) of the traction tower 100 about rotation axis A1. The rotation D of the rotation joint 5/arm assembly about the rotation axis A1 (see, e.g., FIG. 6) can be incremental and locked/unlocked via a slotted/tooth embodiment, as shown and described with respect to an additional rotation functionality (see also discussion with respect to FIGS. 18D-E), can be non-incremental when locked/unlocked via frictional engagement, or can be locked/unlocked via other known lock/unlock mechanisms (as should be understood by a person of ordinary skill in the art in conjunction with a review of this disclosure). The rotation range is shown by shadow (transparent) arm assembly structures 20 positioned around the starting or zero position shown by a solid arm assembly structure 30. The position of the screw (not shown) that holds the traction scale at 7-5 remains consistent despite the rotation of the other portions of the arm assembly. As shown in FIG. 8, a large portion of the arm assembly is offset from a patient's arm when in use, regardless of the arm assembly's rotation position, which creates sufficient space for surgical instruments. Stated differently, this structural configuration and associated functionality allows a medical practitioner to move the arm assembly around the patient's hand without affecting the position or traction of the hand itself. The ability to rotate the arm assembly can be important because if the medical practitioner needs more space around the outside of the wrist joint for medical instruments, the medical practitioner can just swing the arm assembly around to the back of the arm. Another use of this structural feature includes allowing the medical practitioner to maneuver the arm assembly in order to get a c-arm (x-ray machine) into position to take an x-ray while the wrist remains in traction.

Figure 9:
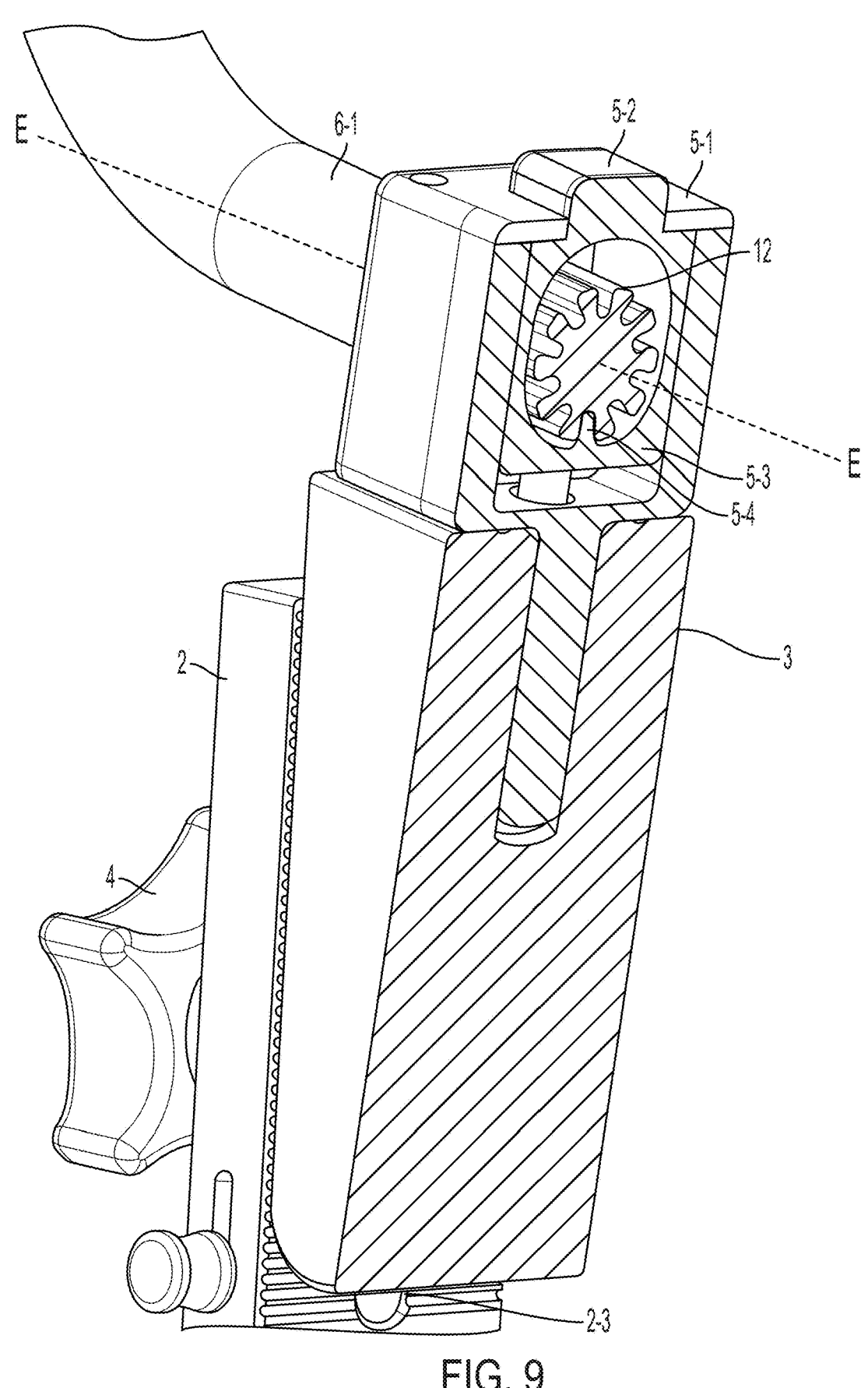
FIG. 9 is a close up partially sectioned perspective view of a lower portion of the traction tower shown in FIG. 1, according to an embodiment.
Figure 10:
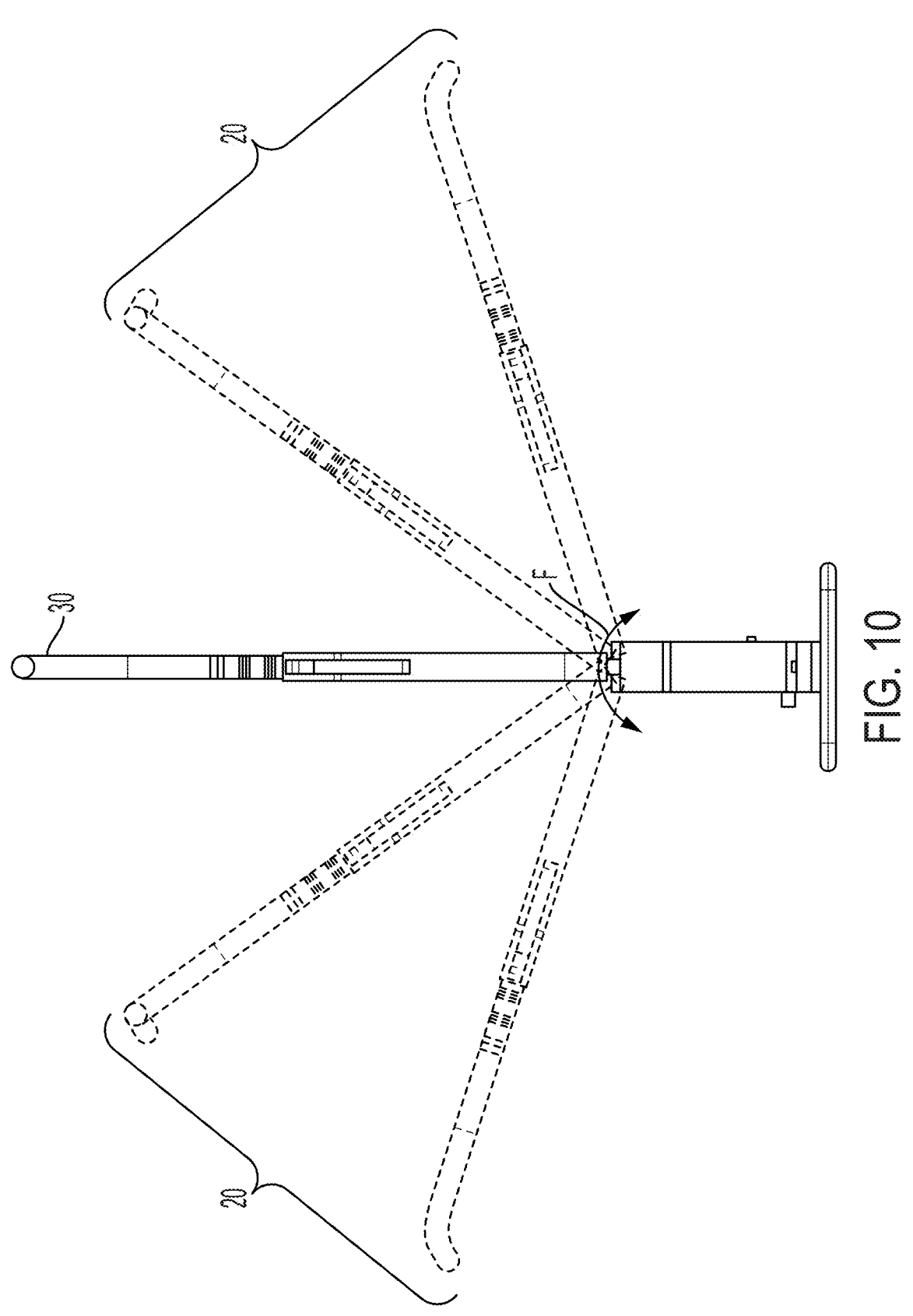
FIG. 10 is a perspective view schematic representation of the traction tower shown in FIG. 1, according to an embodiment.
Figure 11:
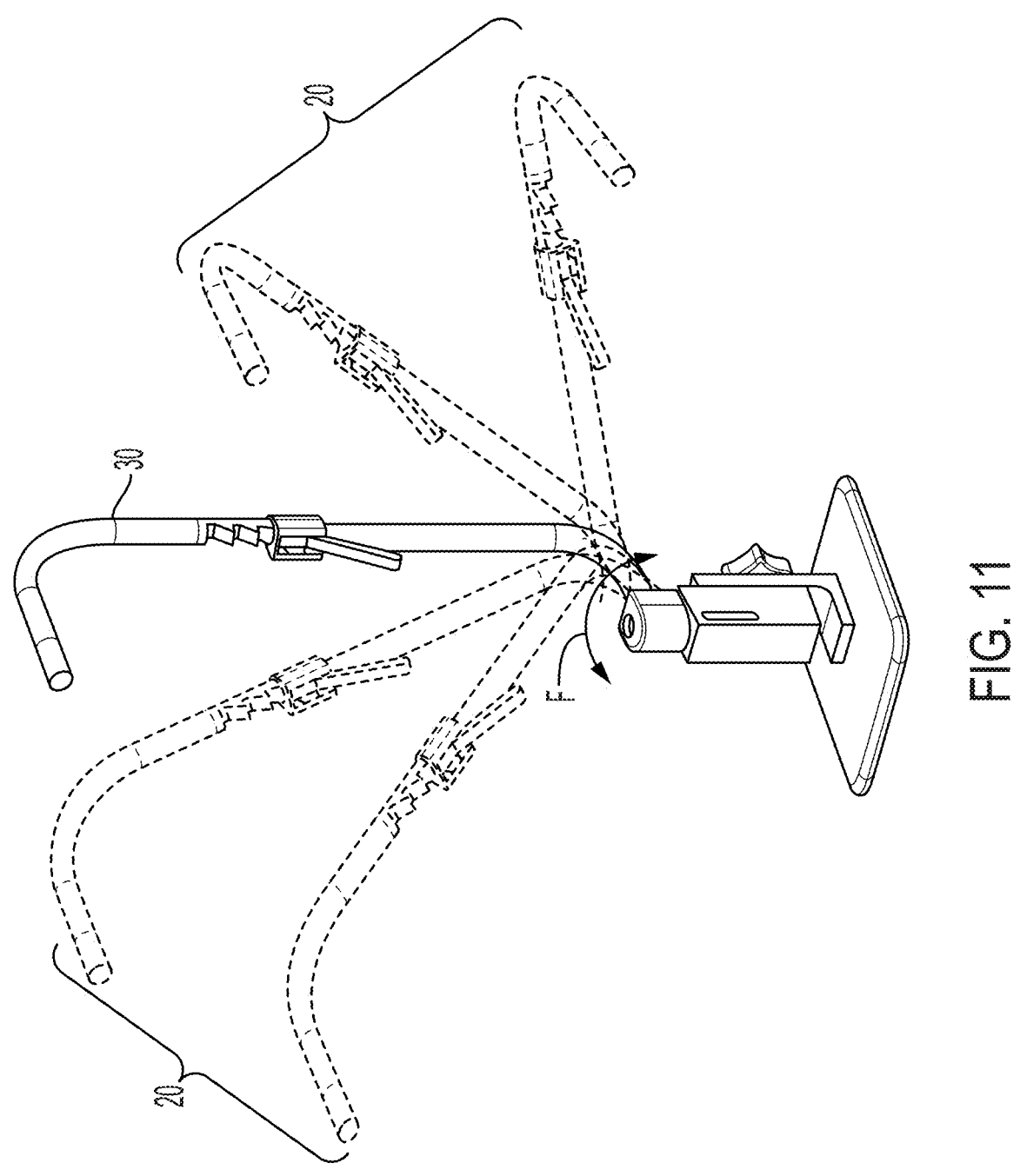
FIG. 11 is a perspective view schematic representation of the traction tower shown in FIG. 1, according to an embodiment.

Turning to FIG. 9, a close up partially sectioned perspective view of a lower portion of the traction tower 100 is shown, according to an embodiment. The interface between the slotted base end 12 of the elongated lower end 6-1 of the lower arm 6 and the rotation joint 5 is shown. In particular, the slots/teeth formed on the slotted base end 12 allow for incremental rotation of the arm assembly around a second rotation axis E - - - E as shown in FIGS. 10 and 11. A main purpose of the rotation of the elongated lower end 6-1 of the lower arm 6 around the second rotation axis E - - - E is to allow the medical practitioner to control the angle of the patient's wrist while in use by keeping the patient's forearm vertical and pulling traction to the hand at an angle from an elongated axis positioned through the patient's forearm (or vertically), as should be understood by a person of ordinary skill in the art in conjunction with a review of this disclosure. In order to be able to rotate the arm assembly around the second rotation axis E - - - E, a button 5-2 can be pushed (force exerted against the button 5-2 opposite the spring bias force) to overcome a bias force exerted by a spring (not shown) up against the button housing 5-3 in the direction of the button 5-2 downward to remove a locking tooth 5-4 from being positioned between two respective slots/teeth of the slotted base end 12. When a desired position of the arm assembly is reached, the force exerted against the button 5-2 by the user can be removed and the arm assembly can be locked into the desired position via the described interlocking mechanism (bias force exerted by the spring pushes the locking tooth 5-4 between another two slots/teeth of the slotted base end 12).

Turning to FIGS. 10 and 11, perspective view schematic representations showing the rotation range of the elongated lower end 6-1 of the lower arm 6 (and, thus, the arm assembly) of the traction tower 100 about rotation axis E - - - E. The rotation F of the elongated lower end 6-1 of the lower arm 6 about the rotation axis E - - - E can be incremental and locked/unlocked via a slotted/tooth embodiment, as shown and described with respect to FIG. 9), can be non-incremental when locked/unlocked via frictional engagement, or can be locked/unlocked via other known lock/unlock mechanisms (as should be understood by a person of ordinary skill in the art in conjunction with a review of this disclosure). An example of the rotation range for wrist angle control is shown by shadow (transparent) arm assembly structures 20 positioned around the starting or zero position shown by a solid arm assembly structure 30.

Figure 12:
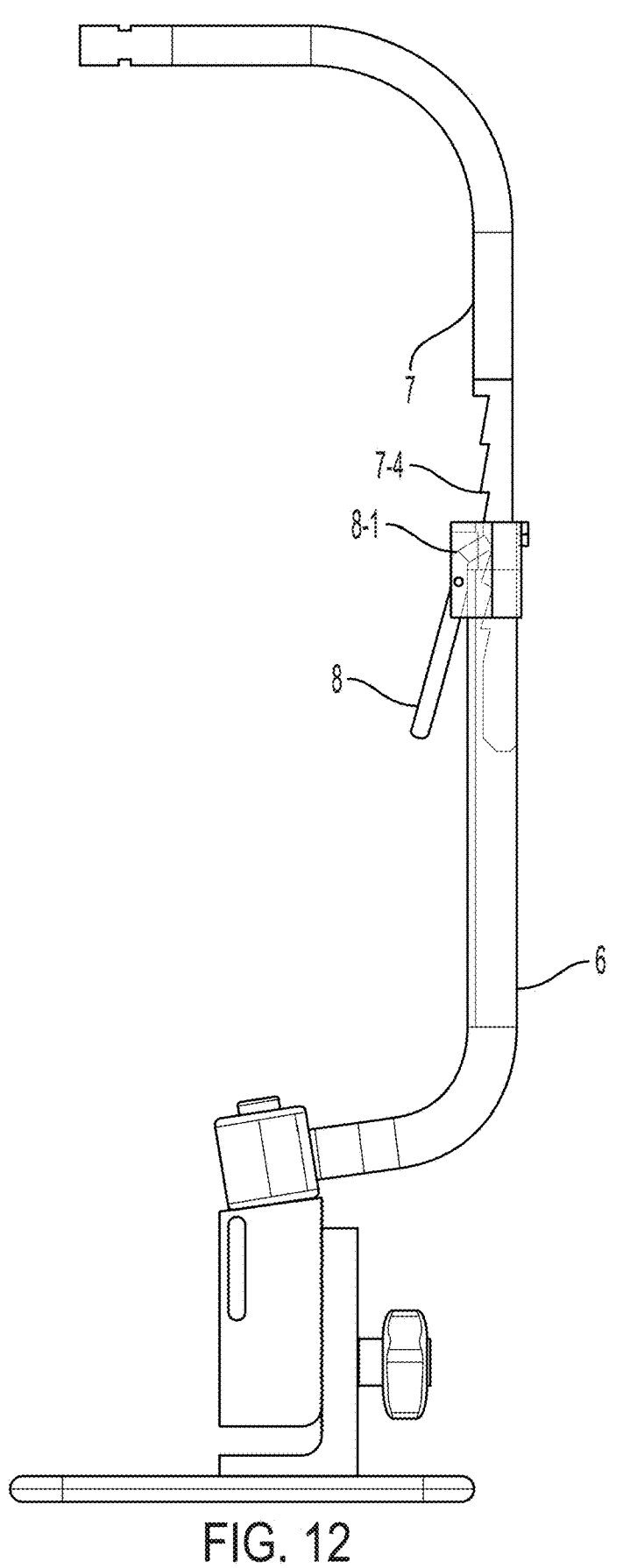
FIG. 12 is a perspective view schematic representation of the traction tower shown in FIG. 1, according to an embodiment.

Referring to FIG. 12, a perspective view schematic representation of the traction tower 100 with the lever 8 and ridges 7-4 engagement structure and resulting functionality is shown in a partial transparent view, according to an embodiment. In brief, the height adjustment mechanism is formed between the upper arm 7 and the lower arm 6. This interface between the upper arm 7 and lower arm 6 allows for another adjustment point to be responsive to a wide variety of individual patient arm sizes. The illustrated adjustment mechanism in FIG. 12 includes a ratchet mechanism for quick height adjustment via actuation of lever 8 to position end 8-1 within a selected/particular notch formed in the upper arm 7 at 7-4.

Figure 13:
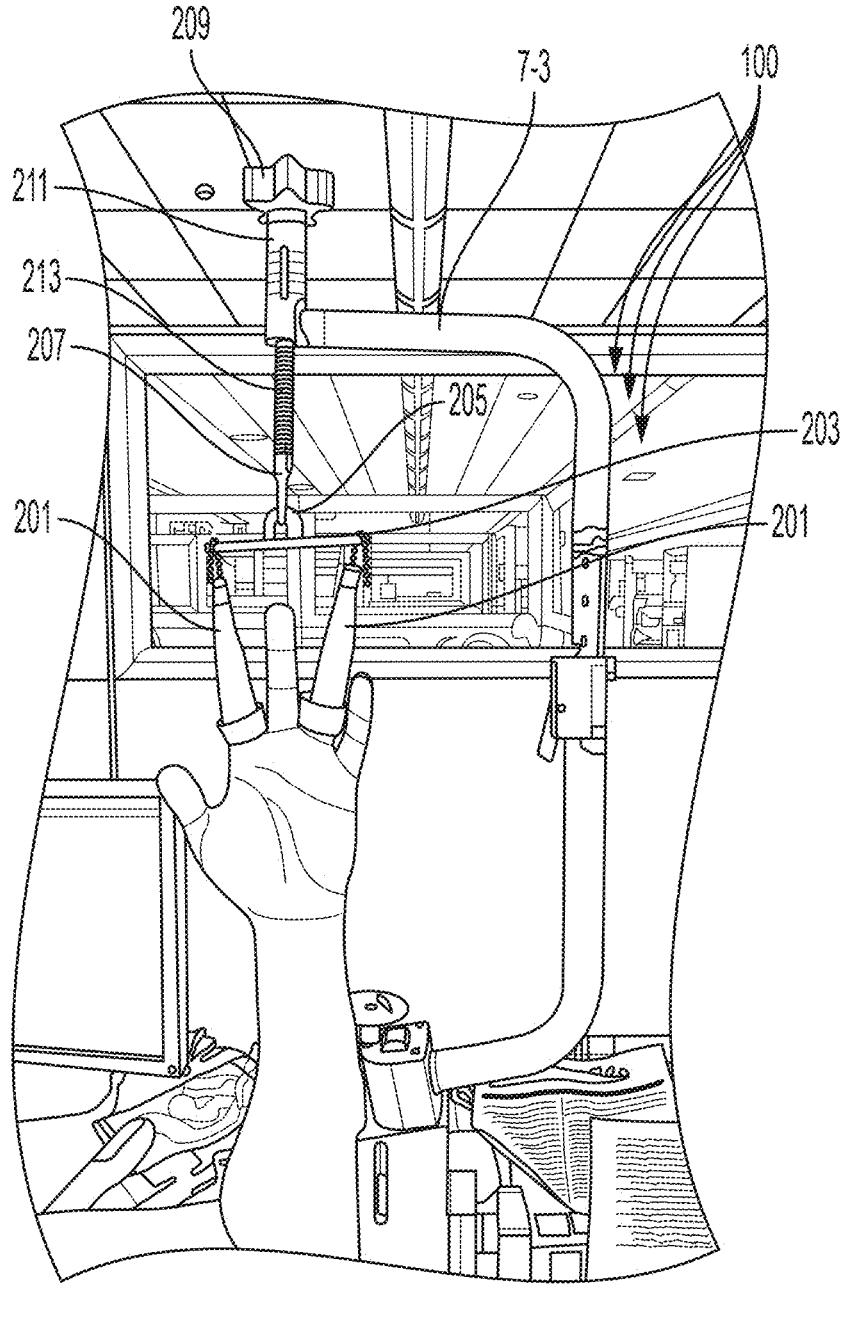
FIG. 13 is a perspective view photographic representation of the traction tower with a traction tower scale, according to an embodiment.
Figures 14A, 14B:
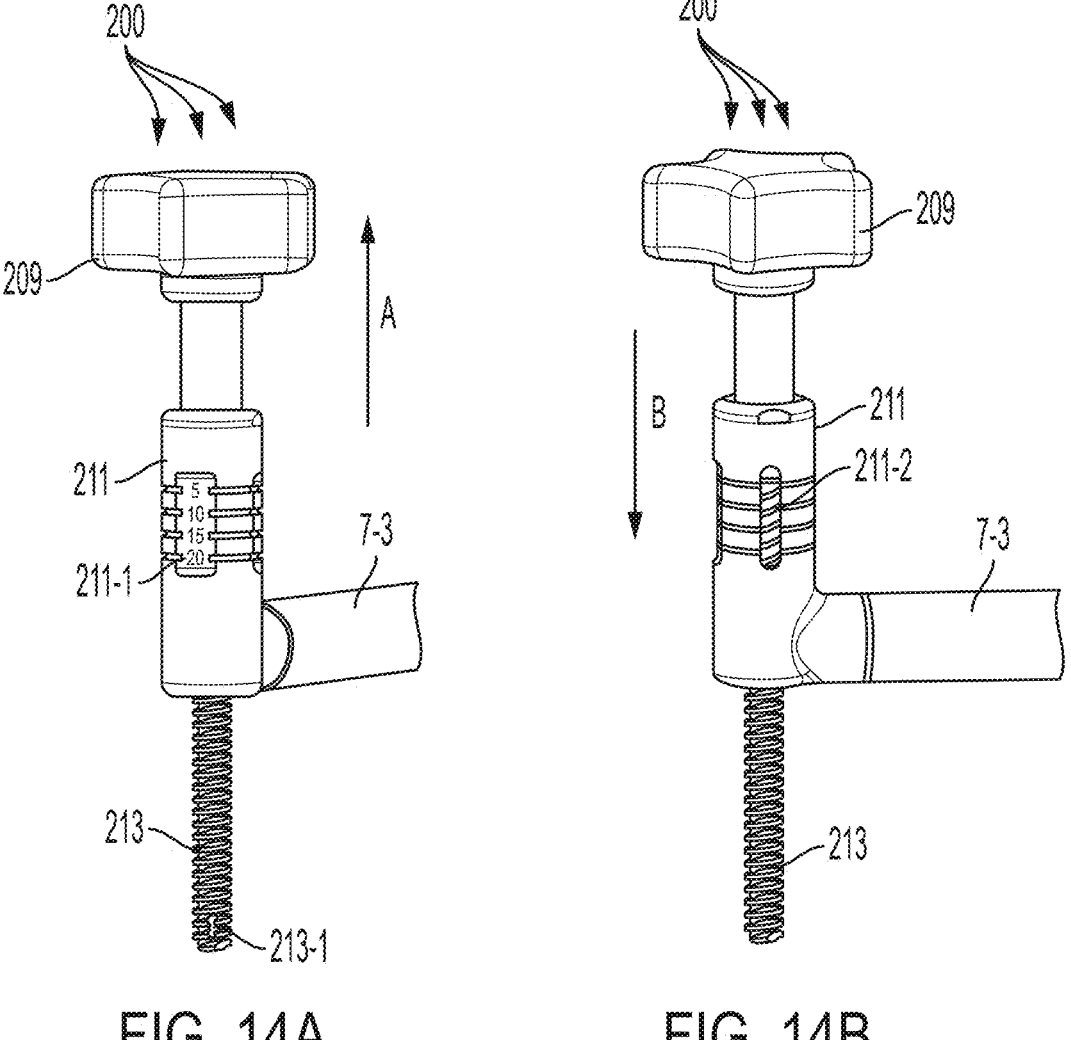
FIG. 14A is a perspective view schematic representation of a traction tower scale, according to an embodiment.
FIG. 14B is a perspective view schematic representation of the traction tower scale shown in FIG. 14A, according to an embodiment.

FIGS. 13-14B illustrate a traction tower scale 200, according to an embodiment. Referring to FIG. 13, a perspective view photographic representation of the traction tower 100 is shown with the traction tower scale 200. The traction tower 200 includes, but is not limited to, a tubular body 211 attached to the distal end of the upper end 7-3 of the upper arm 7 (via welding, screw, nut and bolt or other known attachment means as should be understood by a person of skill in the art in conjunction with a review of this disclosure) of the traction tower 100. The body 211 is configured to contain a knob 209 followed by and attached to a spring (not shown) positioned through the top portion of the body 211. Attached to the bottom end of the spring is a rod/screw 213, which is partially positioned within the body 211 and a portion of which protrudes outside the bottom end of the body 211. The bottom end of the rod/screw 213 includes a hole that receives a clip 207 therethrough. The other end of the clip 207 is attached to a hole formed in or on a rack 203. The rack is shown with two finger traps 201 (but can include one or more than two) attached thereto for securing a patient's fingers and applying traction.

Turning to FIGS. 14A-B, perspective view schematic representations of the traction tower scale 200 are shown, according to an embodiment. The rack 203 (to which the finger traps 201 are attached) is directly linked to the knob 209 through the rod/screw 213 (which can be any type of connection element that can perform the function of the rod/screw 213 described herein, and does not need to be a rod or a screw). In an "at rest" pre-use state (not attached to a patient's fingers, or at least not receiving force from a patient's fingers), the knob 209 is biased in the upward direction (see arrow A) by the spring located in the body (which can be any type of spring including a coil spring with a known biasing force, as should be understood by a person of ordinary skill in the art in conjunction with a review of this disclosure). As a force is applied to the spring in the downward direction (see arrow B) by the weight of a patient's hand/arm (from the finger traps, to the rod/screw

213, to the spring and to the knob 209), the knob 209 (including its stem) will be pulled in the downward direction further into the body 211 of the scale. The stem of the knob 209 can include a visual indicator (e.g., a line or other mark), that can be used to indicate an estimated amount of traction being used. This can be done by viewing where the visual indicator is in the viewing window 211-2, and that location can be matched up with grooves indicating a traction amount number 211-1. The unit of measure for traction is pounds. However, a preferred embodiment uses the traction amount number as a relative reference traction number (e.g., relative traction amount applied to a patients arm/wrist), and not as a specific measurement device.

FIGS. 15-26 collectively illustrate a traction tower 100', according to an alternative embodiment. This alternative embodiment of the traction tower 100' is similar in many respects to traction tower 100 (including structurally and functionally), described above with respect to FIGS. 1-12. As such, the following descriptions of the elements/components of the traction tower 100' are mostly limited to the alternative/different aspects (such as upper tower 3' and rotation joint 5'). If a structural element(s) and its resulting (singular or collective) functionality is not discussed but was illustrated and/or discussed above, the structure and associated functionality is the same as what was discussed above with respect to FIGS. 1-12 and applies in this section (similarly, the discussion with respect to the traction tower scale 200 provided in FIGS. 13-14B applies equally below with respect to the traction tower 200 shown as part of the traction tower 100').

Figure 15:
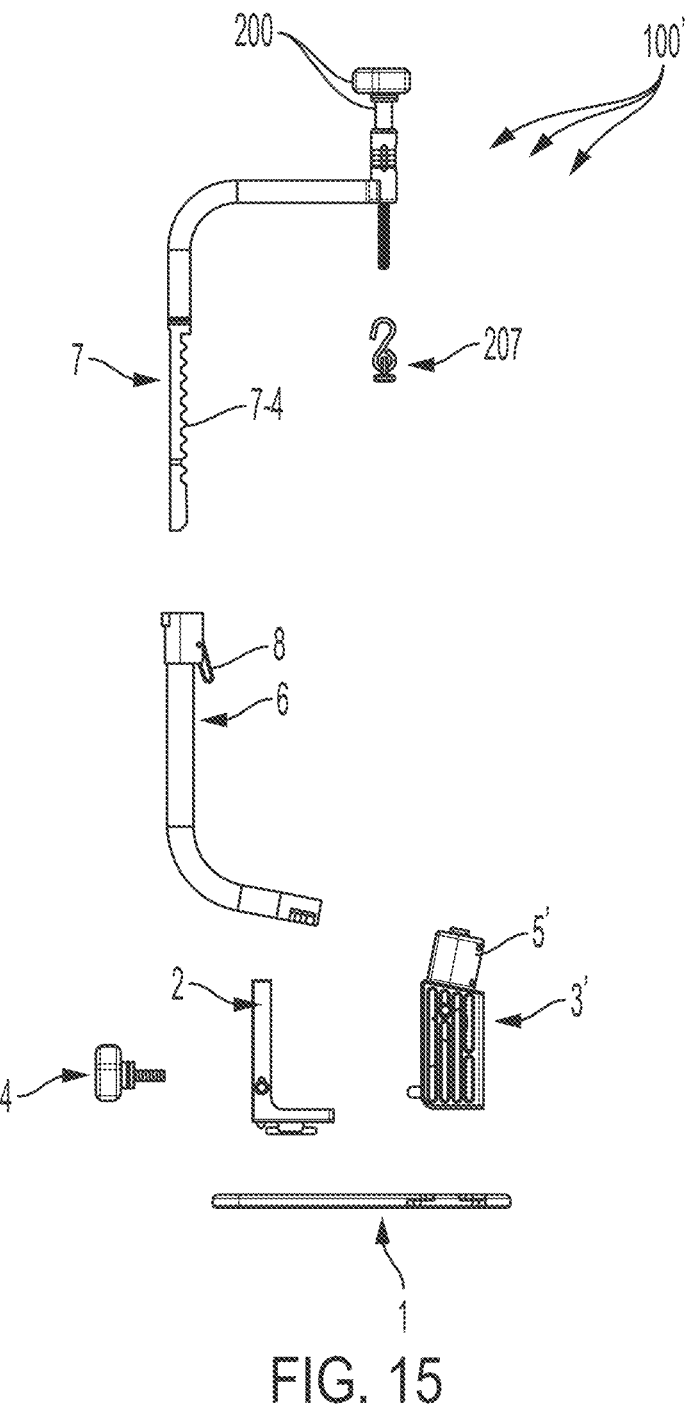
FIG. 15 is an exploded perspective view schematic representation of a traction tower, according to an alternative embodiment.
Figure 16:
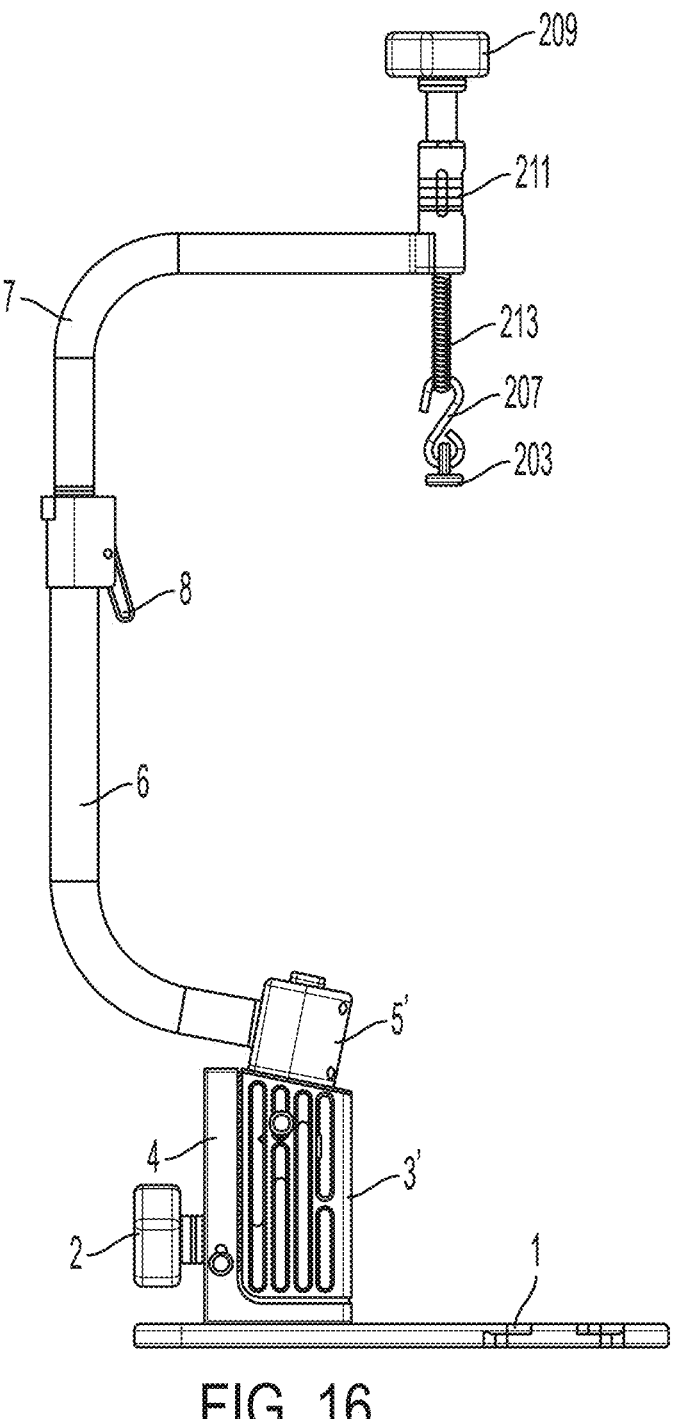
FIG. 16 is an assembled perspective view schematic representation of the traction tower shown in FIG. 15, according to an alternative embodiment.
Figure 17:
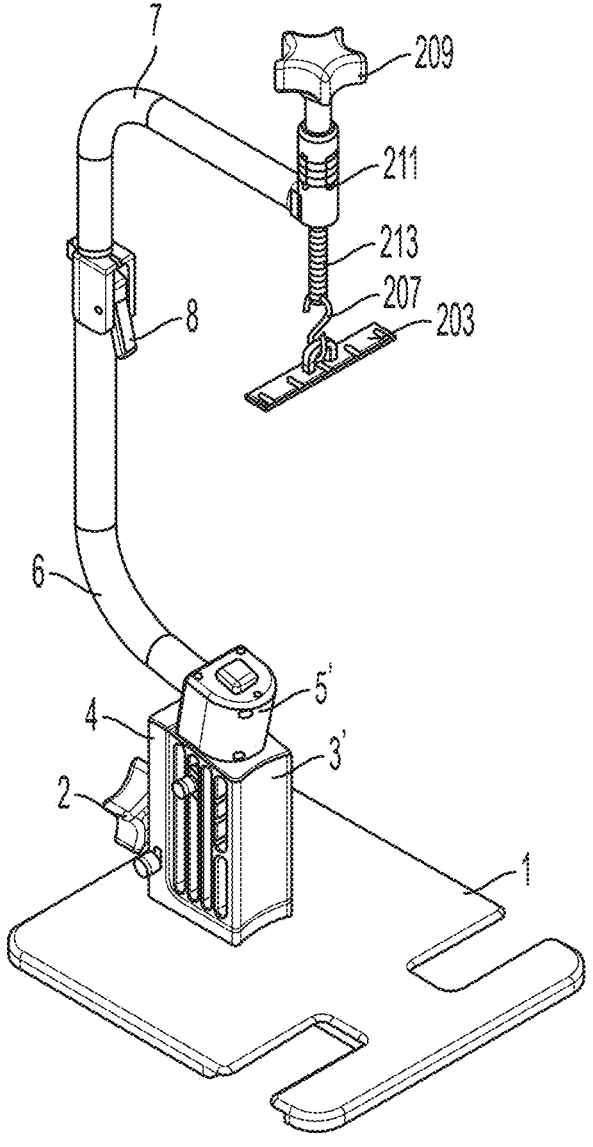
FIG. 17 is an assembled perspective view schematic representation of the traction tower shown in FIG. 15, according to an alternative embodiment.

Turning to FIG. 15, an exploded perspective view schematic representation of a traction tower 100' according to an alternative embodiment is shown. FIG. 15 is similar to FIG. 1, except for the addition of the traction tower 200 (described with respect to FIGS. 13-14B) and the alternative embodiment of the upper tower 3' and the rotation joint 5'. FIGS. 16 and 17 are assembled perspective view schematic representations of the traction tower 100' shown in FIG. 15, according to an alternative embodiment, and are similar to FIGS. 2 and 3, respectively.

Figure 18A:
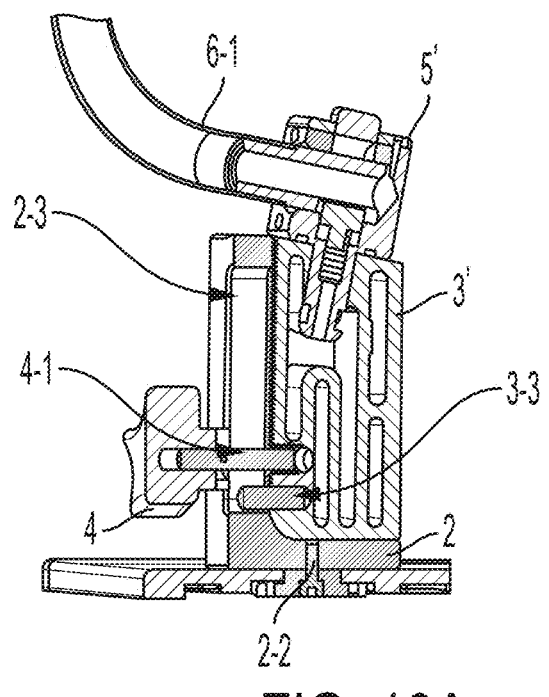
FIG. 18A is a close-up partially sectioned perspective view of a lower portion of the traction tower shown in FIG. 15, according to an alternative embodiment.

FIG. 18A is a close up partially sectioned perspective view of a lower portion of the traction tower 100', according to an alternative embodiment. As previously discussed with respect to FIG. 1, the upper tower 3' includes an alignment peg 3-3, which is configured to fit into a corresponding elongated hole/slot 2-3 in the lower tower 2. Alignment peg 3-3 helps a user easily position the upper tower 3' onto the lower tower 2 before installing the tower locking knob 4. It also makes sure that the upper tower 3' stays vertical if/when a user is adjusting the height of the upper tower 3', because there are two pins/stems in the slot 2-3 of the lower tower (the pin 3-3 from the upper tower 3' and the threaded rod/stem 4-1 from the tower locking knob 4). This way, if the height of the upper tower 3' is adjusted after the full tower is assembled, there is no risk of the whole upper portion (arm assembly) of the tower 100' rotating and swinging down when the tower locking knob 4 is loosened. In this embodiment, height adjustment can be done with the tower locking knob 4 loosened, not removed entirely from the lower tower/upper tower.

Figure 18B:
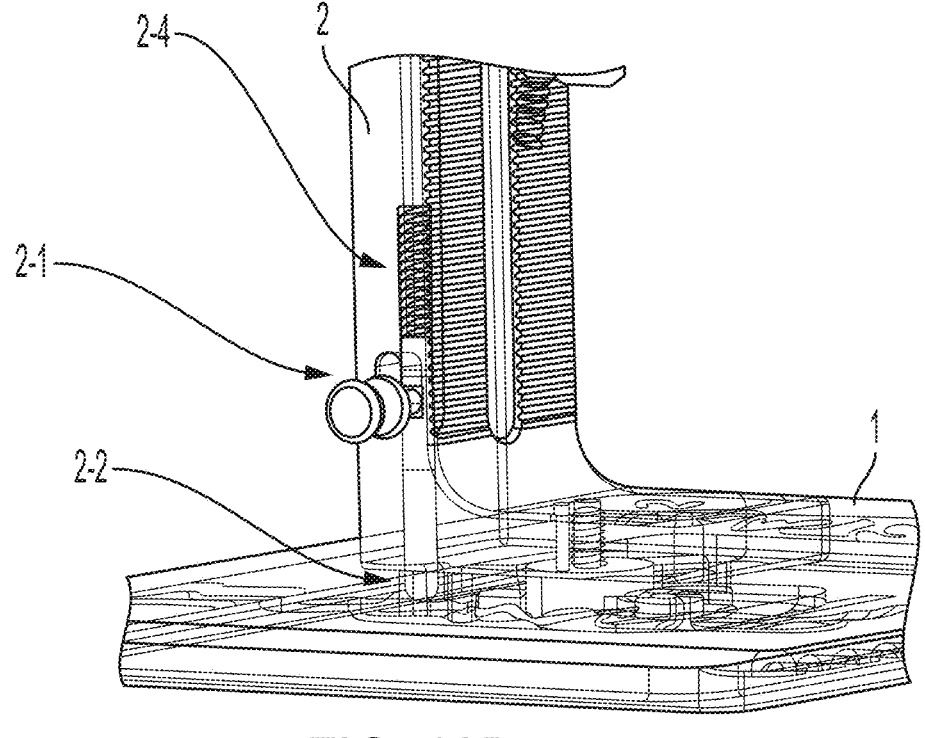
FIG. 18B is a close-up transparent perspective view of a lower portion of the traction tower shown in FIG. 15, according to an alternative embodiment.
Figure 18C:
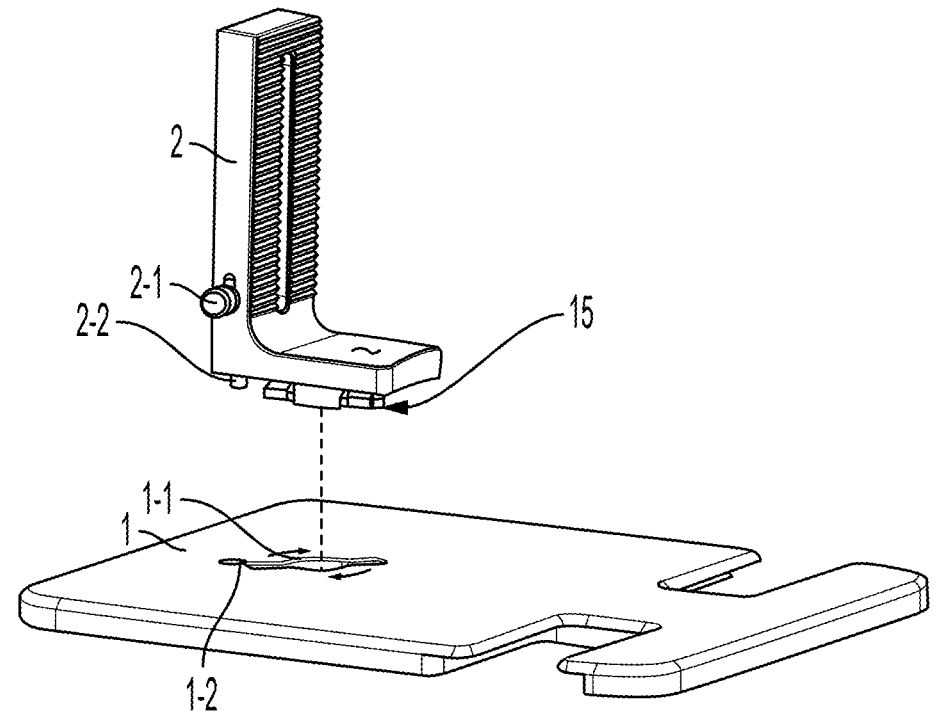
FIG. 18C is a close-up solid view of a lower portion of the traction tower shown in FIG. 15, according to an alternative embodiment.

Turning to FIG. 18B-C, a close up transparent perspective view and a solid view, respectively, of a lower portion of the traction tower 100' is shown, according to an alternative embodiment. The lower tower 2 includes a sliding button 2-1, which is attached to locking peg 2-2. Spring 2-4 biases sliding button 2-1 and peg 2-2 in the downward direction, which can be overcome by a user sliding button 2-1 up moving peg 2-2 within the body of lower tower 2. The purpose of peg 2-2 and attachment means 15 (here a key locking feature) is to lock the lower tower 2 into the base plate 1 when it is installed and to make sure it doesn't move until the tower 100' is ready to be disassembled. It also allows the user to quickly assemble and passively lock it in place when assembling the tower 100' (since peg 2-2 is spring biased to the downward position, the slider button 2-1 does not have to be actuated when assembling—lower tower 2 can just be pushed flush to the base 1 and twisted causing peg 2-2 to fall into base hole 1 when it is at the right rotation position). The key locking feature 15 is placed onto base keyhole 1-1 at the same time to assist with the locking of the lower tower 2 to the base 1 after the twisting motion.

Figure 18D:
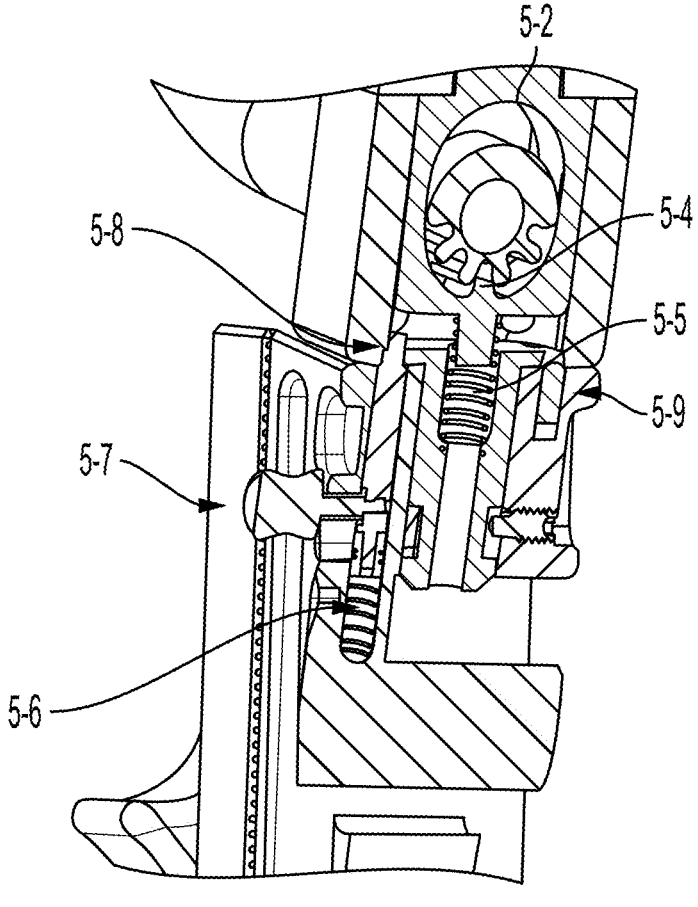
FIG. 18D is a close-up partially sectioned perspective view of a lower portion of the traction tower shown in FIG. 15, according to an alternative embodiment.
Figure 18E:
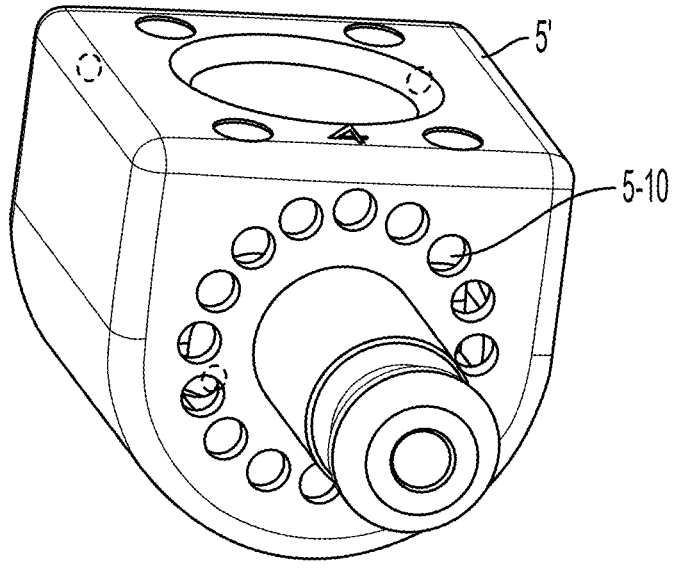
FIG. 18E is a close-up bottom perspective view of the rotation joint of the traction tower shown in FIG. 15, according to an alternative embodiment.

Turning to FIG. 18D, a close up partially sectioned perspective view of a lower portion of the traction tower 100' is shown, according to an alternative embodiment. A slider button 5-7 is shown connected to a locking peg 5-8, which is biased up via spring 5-6 into a hole 5-10 formed into the body of rotation joint 5. To release and freely rotate rotation joint around rotation axis A1, a user can push slider button 5-7 in the downward direction to remove the locking peg from the hole 5-10 until the desired rotation position is reached. Then the button can be released, and the spring 5-6 can move the locking peg 5-8 into another hole 5-10 (see FIG. 18E).

Figure 19:
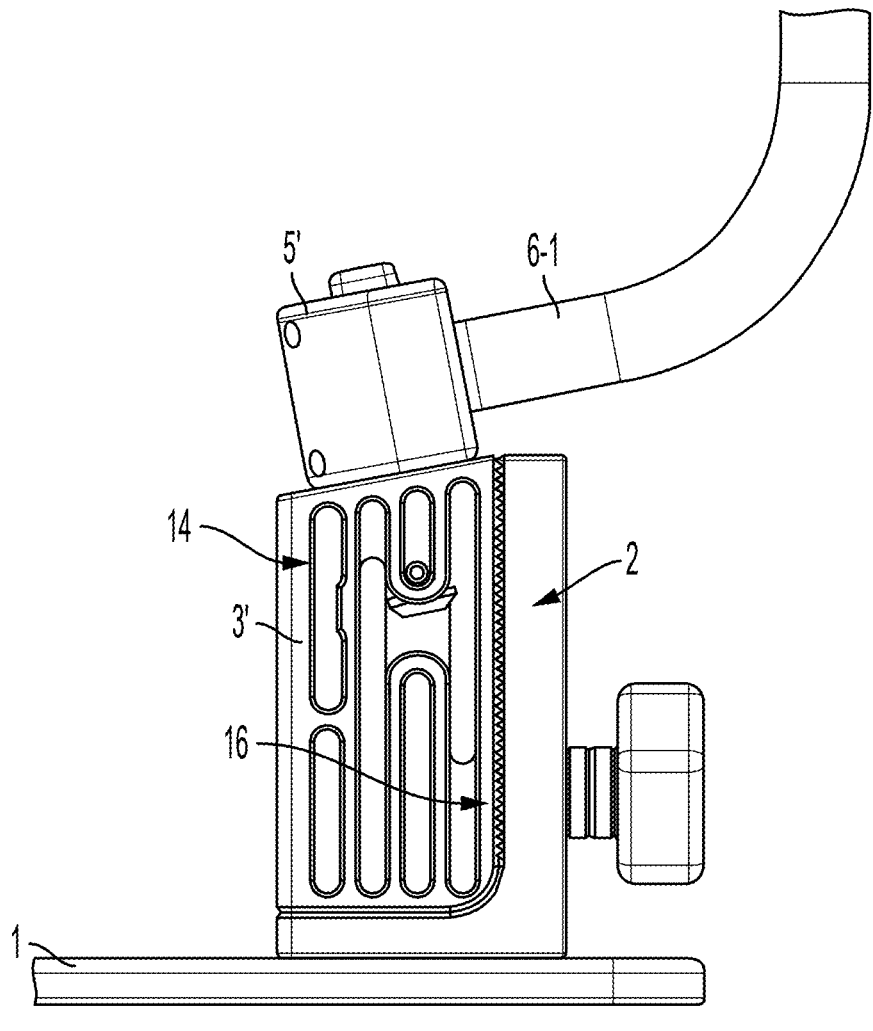
FIG. 19 is a close-up perspective view schematic representation of a lower portion of the traction tower shown in FIG. 15, according to an alternative embodiment.
Figure 20:
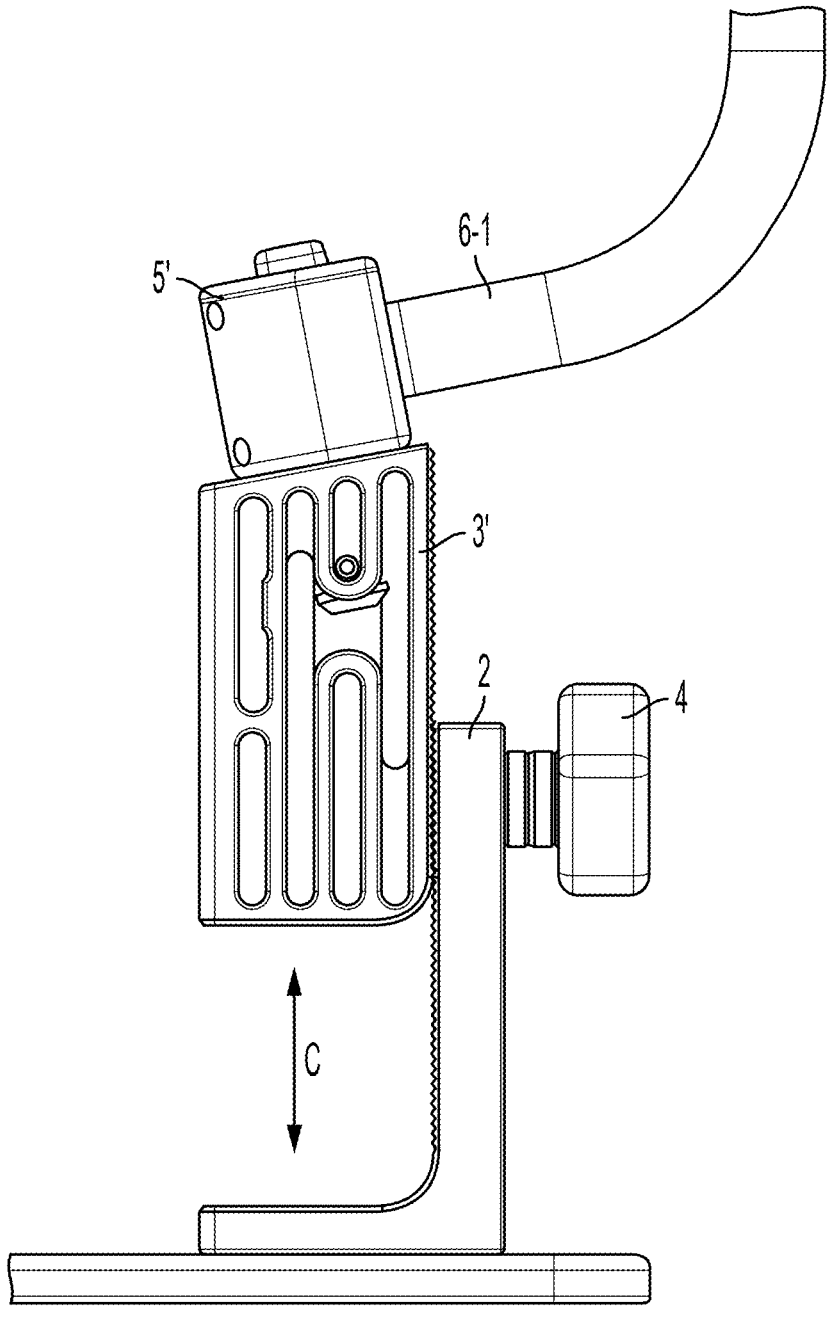
FIG. 20 is a close-up perspective view schematic representation of a lower portion of the traction tower shown in FIG. 15, according to an alternative embodiment.

Turning to FIGS. 19 and 20, close up perspective view schematic representations of a lower portion of the traction tower 100' shown in FIG. 15 are provided, according to an alternative embodiment. FIGS. 19 and 20 are similar to FIGS. 4-5, except for the structural differences noted with respect to the discussion herein and above regarding rotation joint 5' and upper tower 3'. However, the same movement of upper tower 3 with respect to lower tower 2 to accommodate a variety of individual patent forearm sizes, and the structural features that allow for such movement, are present in upper tower 3'. FIG. 19 shows the upper tower 3' in its relatively lowest position with respect to lower tower 2, and FIG. 20 shows the upper tower 3' in its relatively highest position with respect to the lower tower 2. The apertures shown other than aperture 14 show where metal has been removed for weight reduction and heat management purposes.

Figure 21:
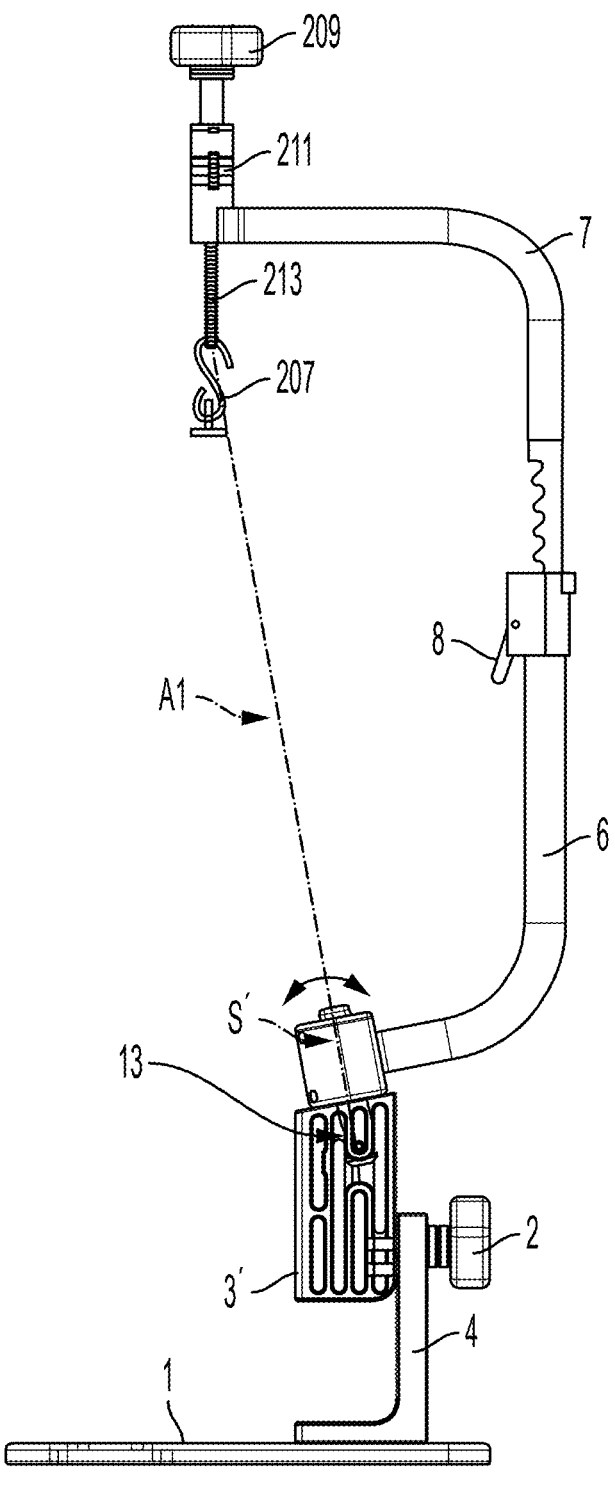
FIG. 21 is a perspective view schematic representation of the traction tower shown in FIG. 15, according to an alternative embodiment.

Referring to FIG. 21, a perspective view schematic representation of the traction tower 100' shown in FIG. 15 is provided, according to an alternative embodiment. Similar to FIG. 6, FIG. 21 shows the rotation axis A1 created by angling the rotation joint 5' positioned on and its stem 13 positioned within upper tower 3'.

Figure 22:
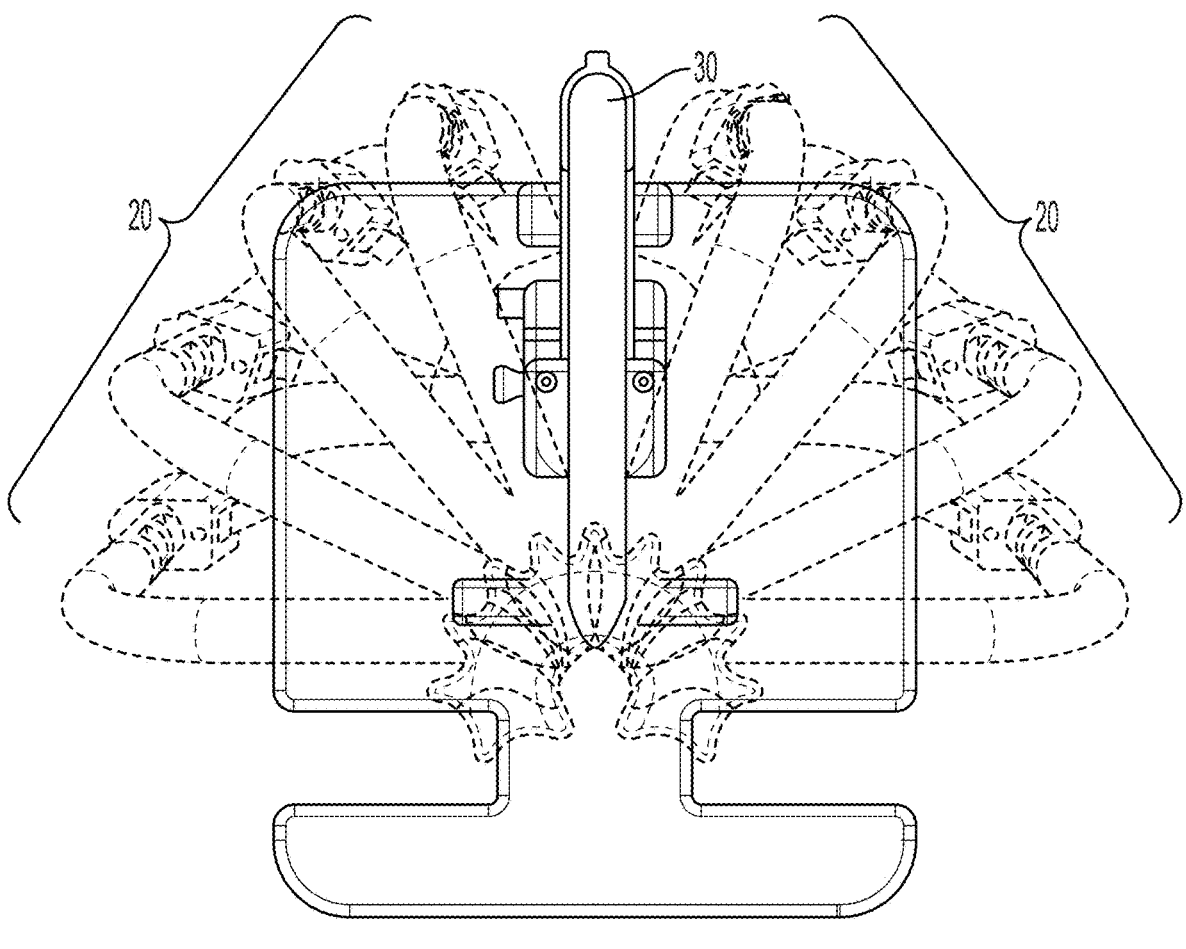
FIG. 22 is a perspective view schematic representation of the traction tower shown in FIG. 15, according to an alternative embodiment.
Figure 23:
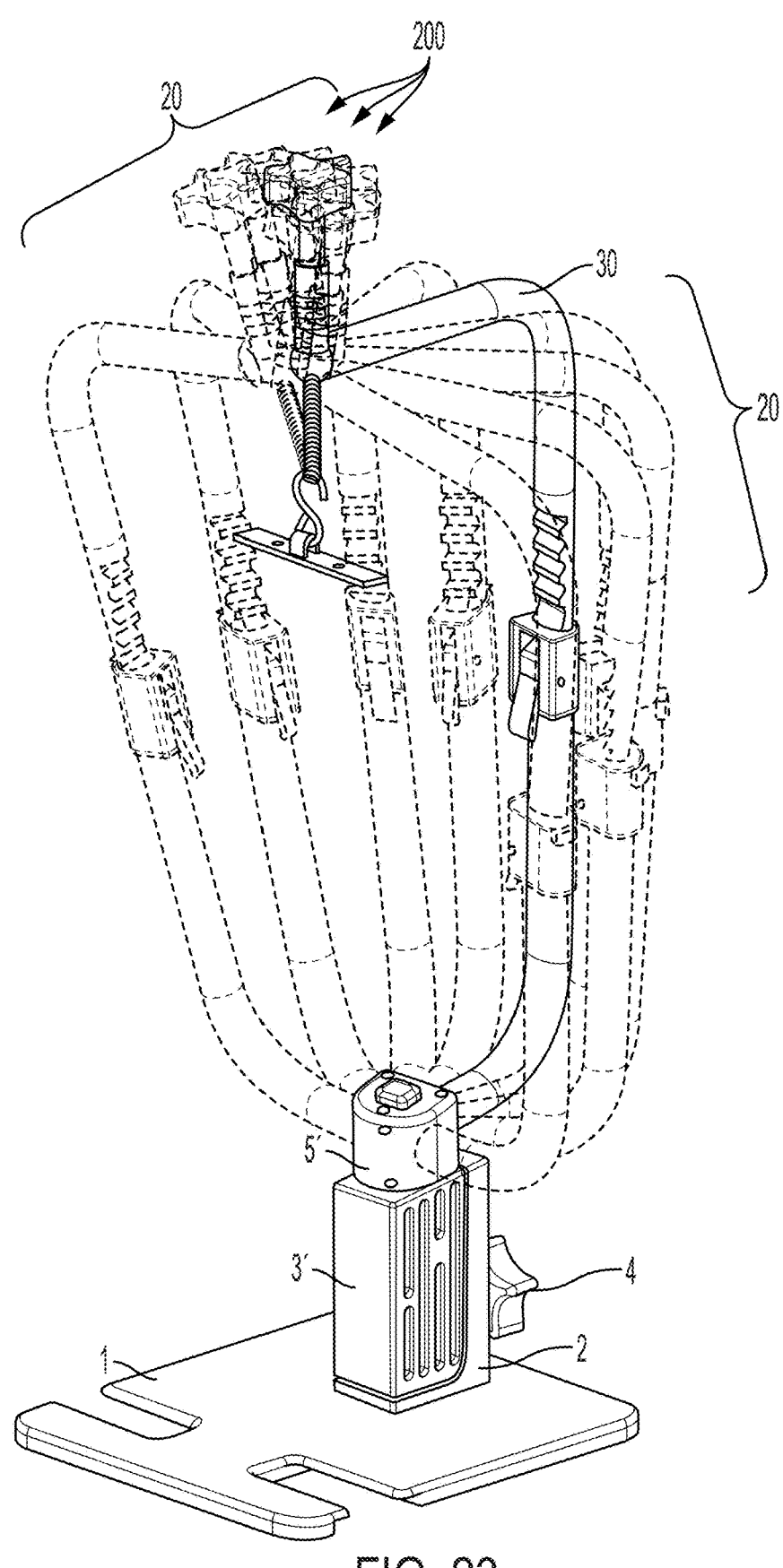
FIG. 23 is a top view schematic representation of the traction tower shown in FIG. 15, according to an alternative embodiment.

Turning to FIGS. 22 and 23, perspective and top view schematic representations showing the rotation range of rotation joint 5 (and, thus, the arm assembly) of the traction tower 100' about rotation axis A1 are provided. FIGS. 22 and 23 are similar to FIGS. 22 and 23, respectively.

Figure 24:
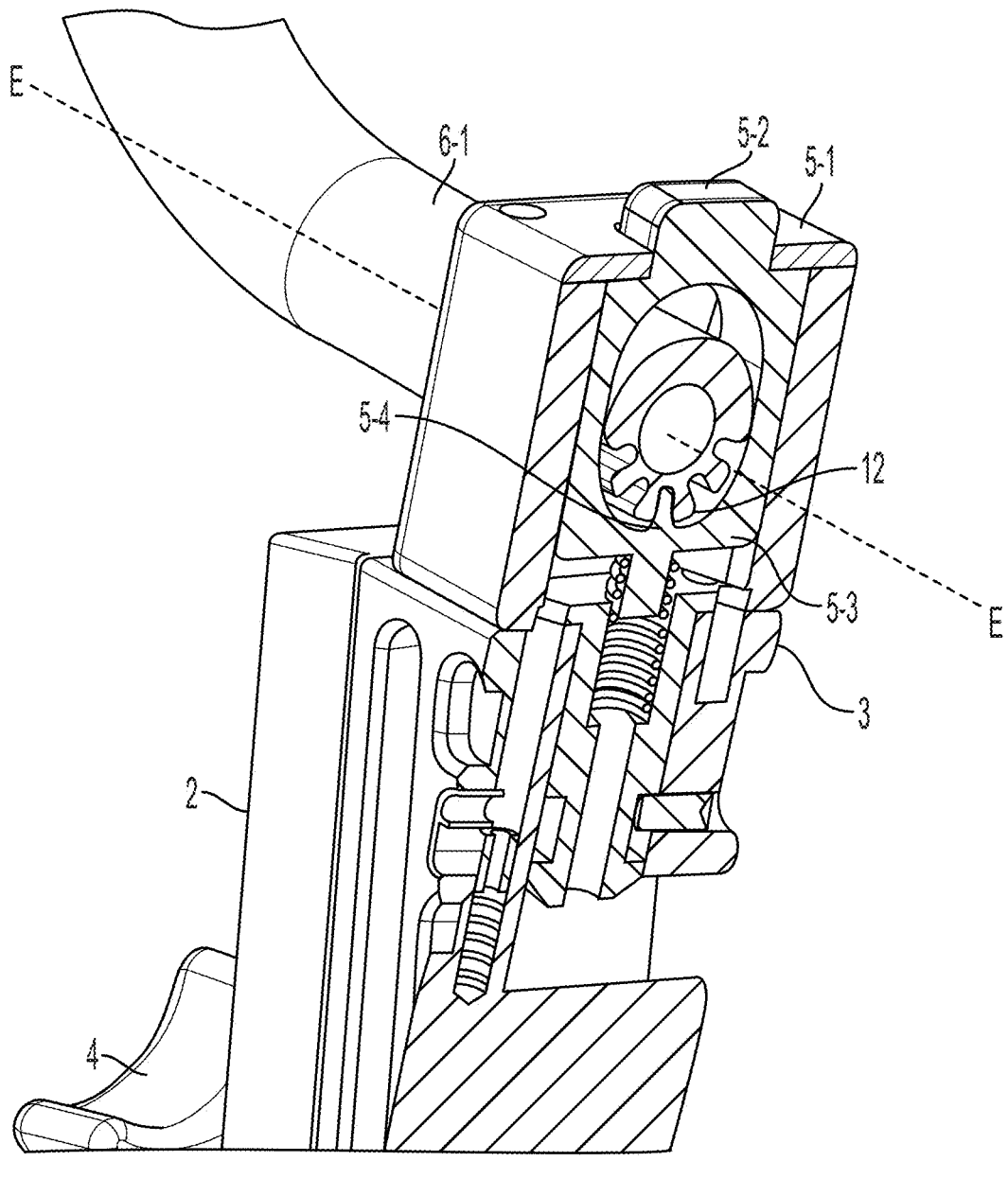
FIG. 24 is a close-up partially sectioned perspective view of a lower portion of the traction tower shown in FIG. 15, according to an embodiment.

Referring to FIG. 24, a close up partially sectioned perspective view of a lower portion of the traction tower 100' is shown, according to an embodiment. FIG. 24 is similar to FIG. 9, and the elements function in a similar manner even though there are some structural differences with respect to rotation joint 5' and upper tower 3', discussed above.

Figure 25:
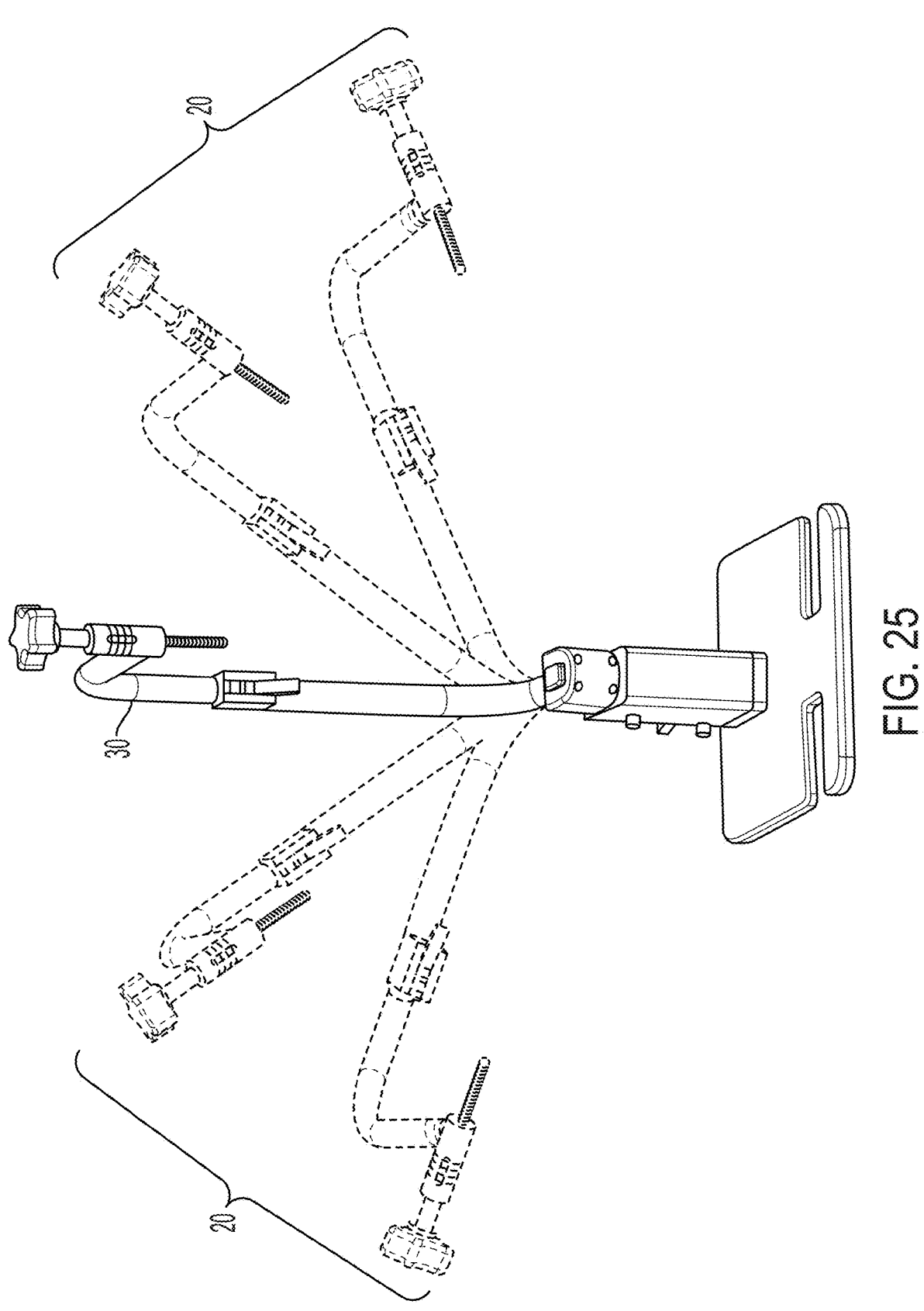
FIG. 25 is a perspective view schematic representation of the traction tower shown in FIG. 15, according to an alternative embodiment.

Referring to FIG. 25, a perspective view schematic representation showing the rotation range of the elongated lower end 6-1 of the lower arm 6 (and, thus, the arm assembly) of the traction tower 100 about rotation axis E - - - E. FIG. 25 is similar to FIGS. 10 and 11.

Figure 26:
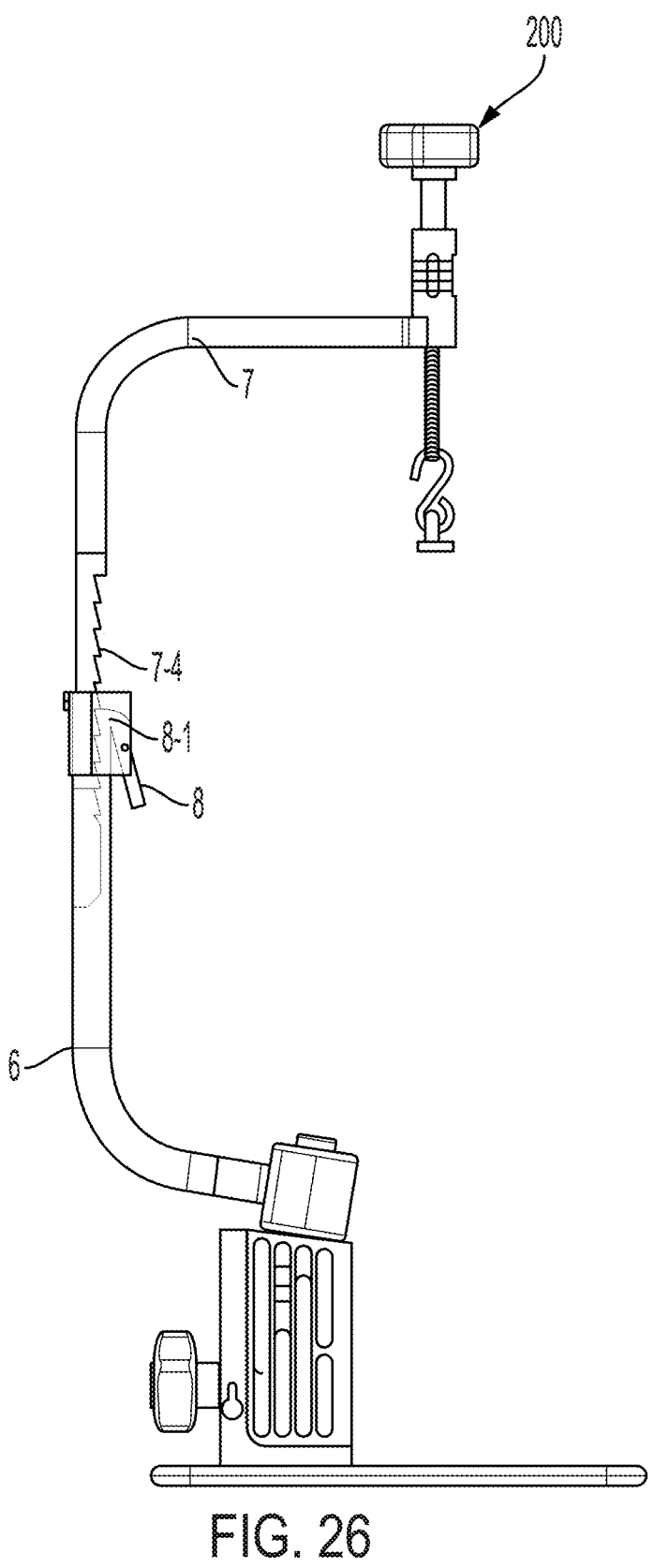
FIG. 26 is a is a perspective view schematic representation of the traction tower shown in FIG. 15, according to an alternative embodiment.

Turning to FIG. 26, a perspective view schematic representation of the traction tower 100' is shown with a height adjustment mechanism including the lever 8 and ridges 7-4 engagement structure and resulting functionality in a partial transparent view, according to an alternative embodiment. FIG. 26 is similar to FIG. 12.

Figure 27:
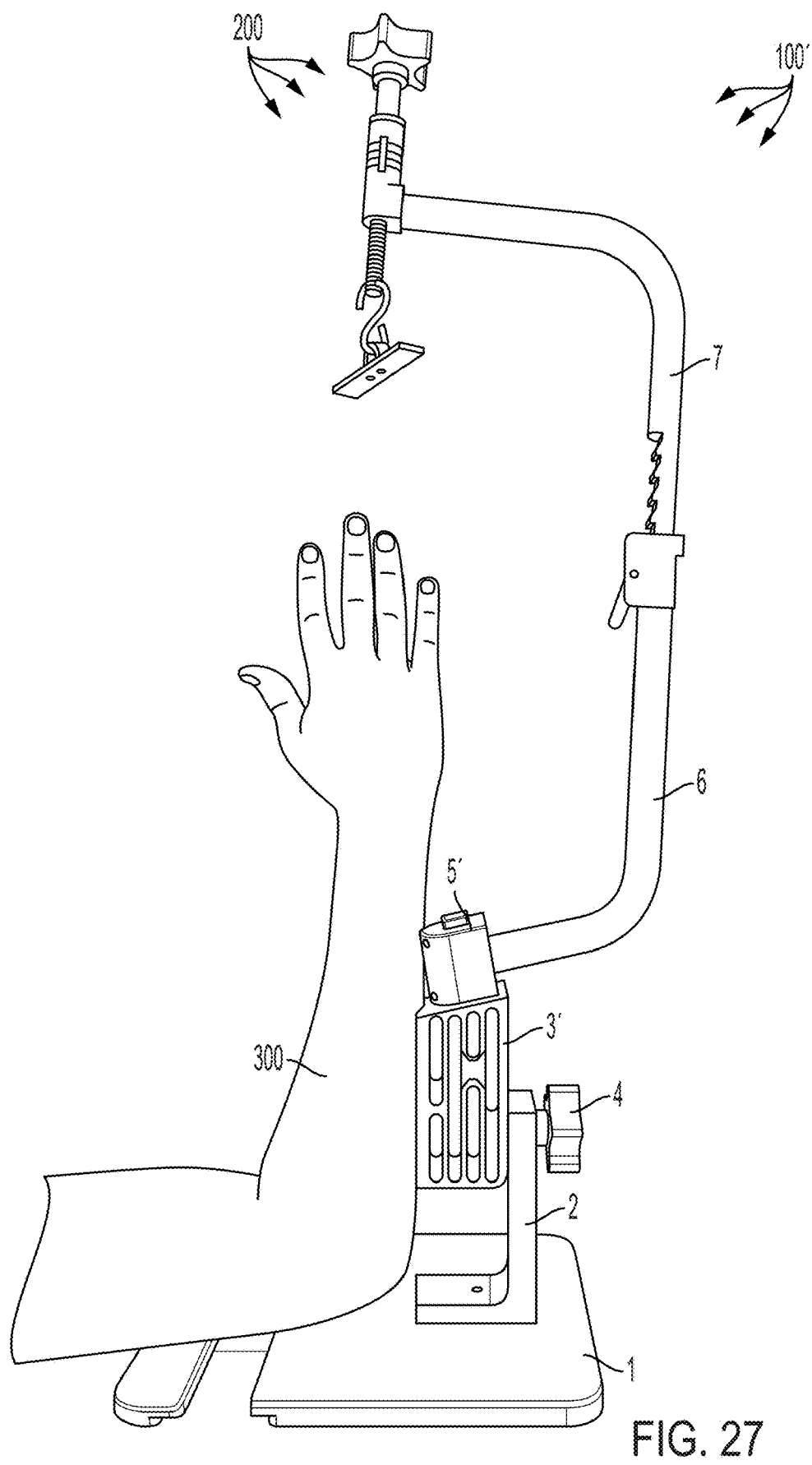
FIG. 27 is a perspective view photographic representation of the traction tower, according to an alternative embodiment.

Turning to FIG. 27, a perspective view photographic representation of the traction tower 100' is shown, according to an alternative embodiment. FIG. 27 shows the placement of a patient's arm with respect to the traction tower assembly 100'.

Figure 28A:
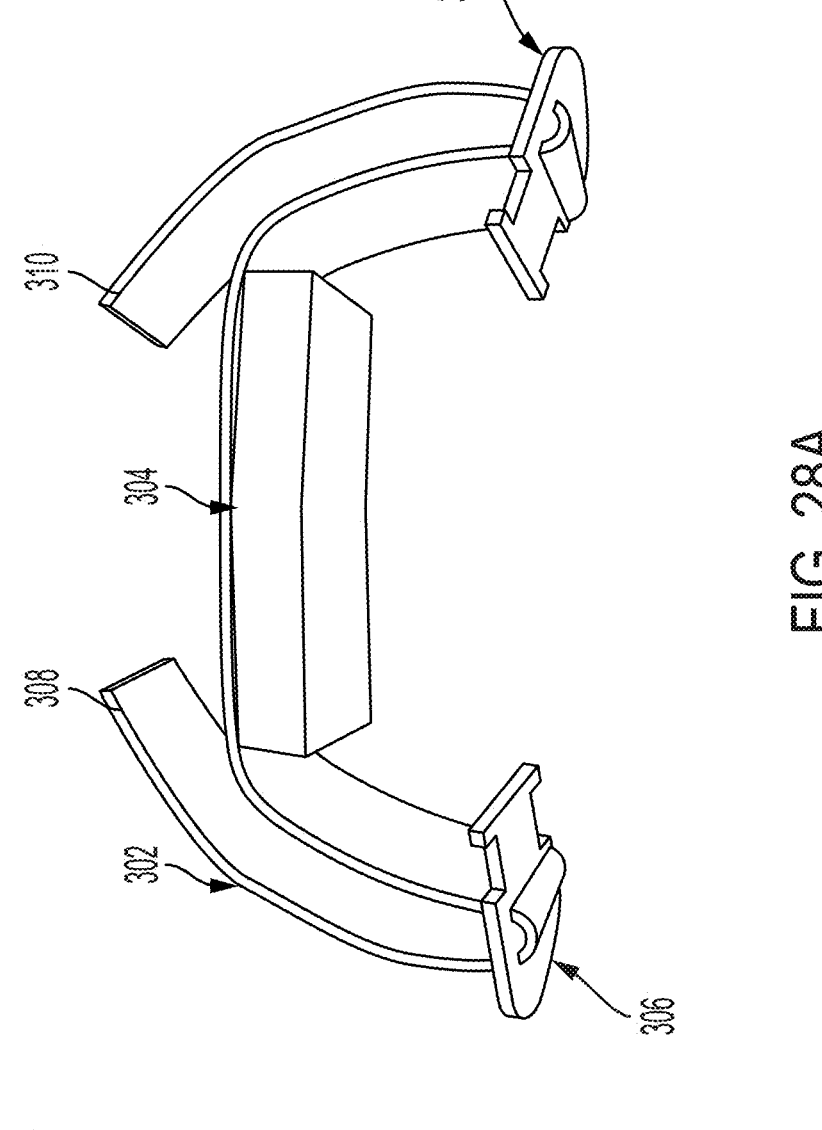
FIG. 28A is a top view photographic representation of a strap, according to an embodiment.
Figure 28B:
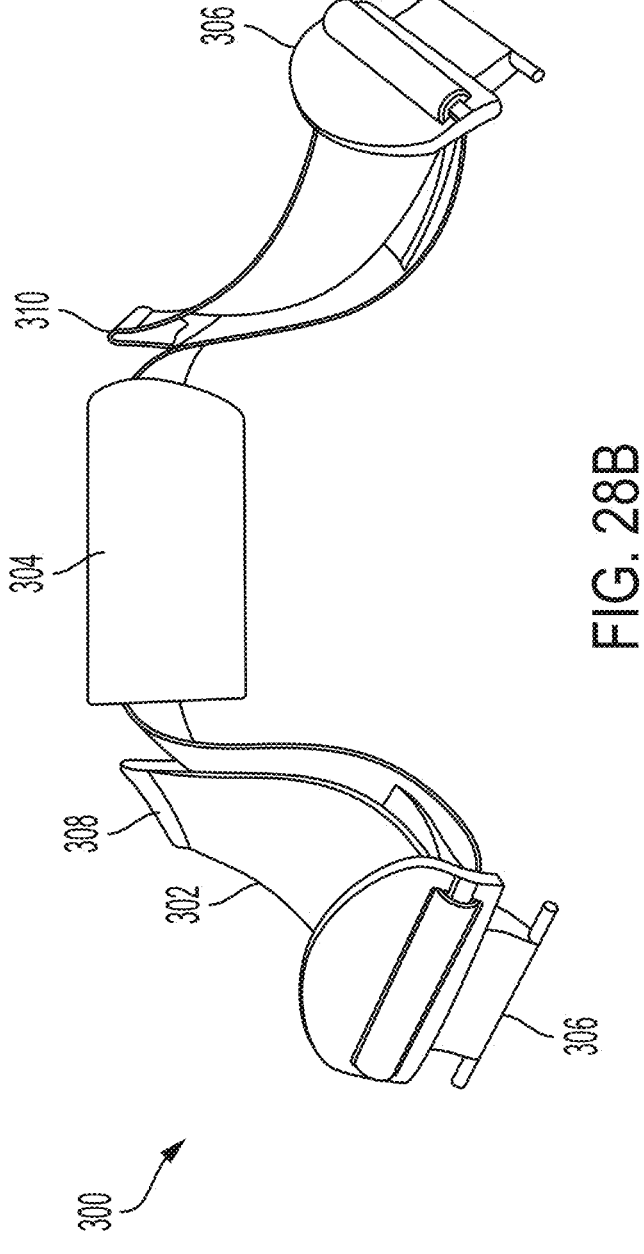
FIG. 28B is a top view photographic representation of a strap, according to an alternative embodiment.

Referring now to FIGS. 28A and 28B, there are shown top views photographic representations of a strap 300, according to two embodiments. The strap 300 is designed for a quick connection to the traction tower 100 and easy adjustment of strap 300 length to accommodate various patient sizes. While the strap 300 can be used to secure the patient's arm at any location, the embodiment of the strap 300 in FIGS. 28A-28B is preferably placed around the patient's bicep. The strap 300 in FIGS. 28A-28B comprises a length of material 302 for wrapping around the patient's arm (e.g., bicep). The length of material 302 can be composed of any non-flexible material, such as polyester, for example. The length of material 302 must be inflexible so as to prevent stretching and loosening around the patient's arm. The length of material 302 should also be composed of a material that is non-irritating to the skin while having enough friction to permit the length of material 302 to lock when in use and glide along itself when released.

Still referring to FIGS. 28A-28B, the length of material 302 comprises a pad 304 for the comfort and safety of the patient. The pad 304 is attached to at least a portion of the length of material 302. In the embodiment in FIG. 28A, the pad 304 has a width that is substantially similar to the width of the length of material 302 such that the pad 304 does not extend beyond the bounds of the length of material 302. In FIG. 28A, the pad 304 is attached to the length of material 302 with adhesive or with connectors, such as hook and loop connectors, to allow for easy replacement of the pad 304.

In the embodiment shown in FIG. 28B, the pad 304 extends around at least a portion of the length of material 302. The strap 300 in FIG. 28B is preferably a bicep strap which is used to hold the patient's biceps to the base plate 1 of the traction tower 100 (hereinafter, the base plate, traction tower, and components thereof can be of any aforementioned embodiment). In FIG. 28B, the pad 304 is cylindrical or tubular. In one embodiment, the pad 304 is a 2-inch-wide webbing with a foam pad to distribute the force to the patient's bicep. The pad 304 can either be fixed around the length of material 302 or it can be detachable (e.g., via a seam along the length of the pad 304 attachable with adhesive or connectors). The cylindrical or tubular pad 304 extending around at least a portion of the length of material 302 allows the pad 304 to move or roll slightly along the arm of the patient. The ability of the pad 304 to move or roll allows for movement of the patient's arm while maintaining the comfort of the pad 304.

Referring to both FIGS. 28A and 28B, the length of material 302 comprises one or more adjustment mechanisms 306. The purpose of the adjustment mechanism 306 is to tighten the strap 300 (i.e., adjust the length of the strap 300) and secure arms of various sizes onto the base plate 1 of the traction tower 100. In the depicted embodiment, the adjustment mechanism 306 is a buckle. Specifically, the length of material 302 in FIGS. 28A-28B has two buckles 306, one on each side of the pad 304.

Figure 29A:
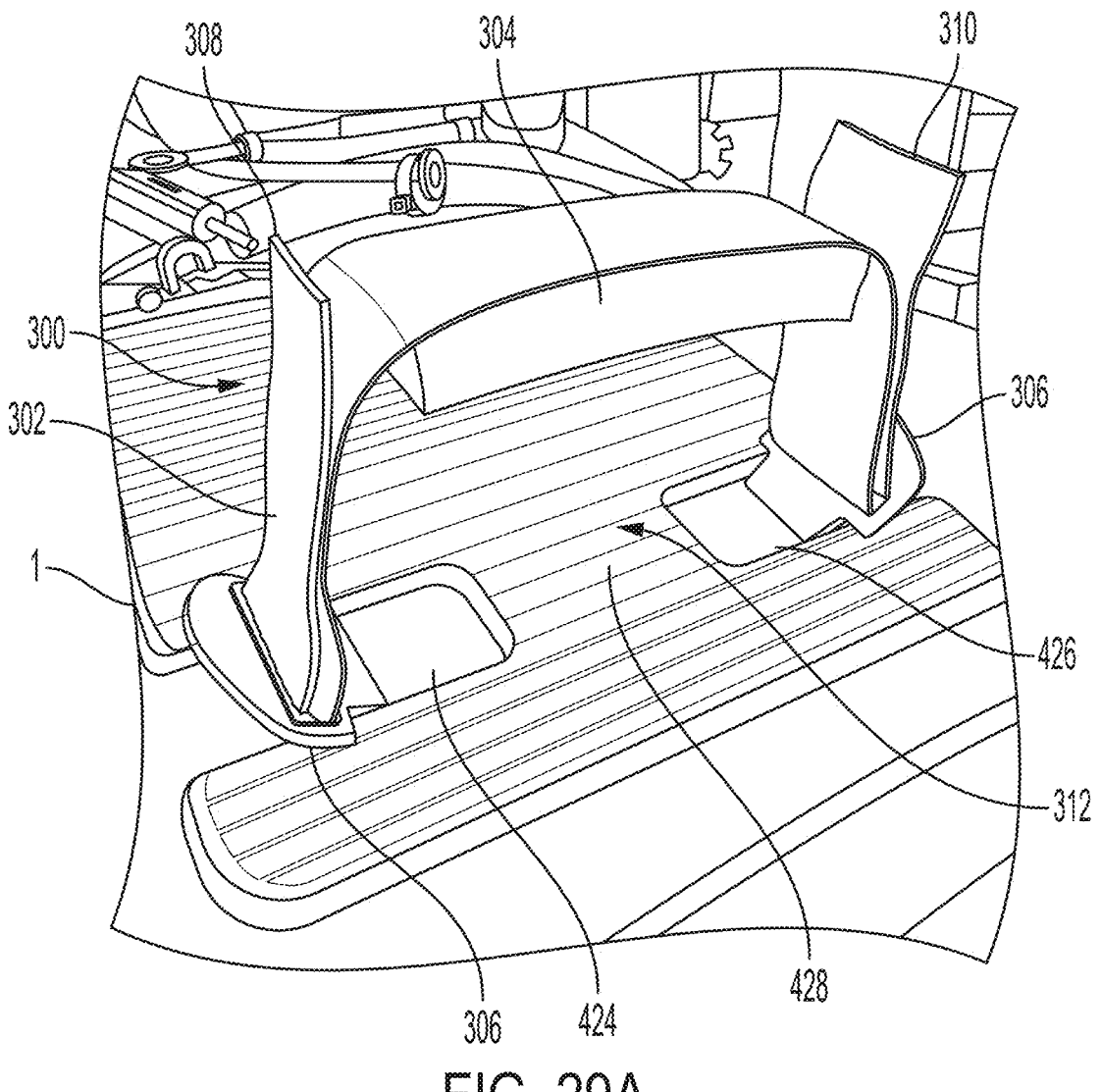
FIG. 29A is a perspective view photographic representation of the strap connected to a base plate of the traction tower, according to an embodiment.
Figure 29B:
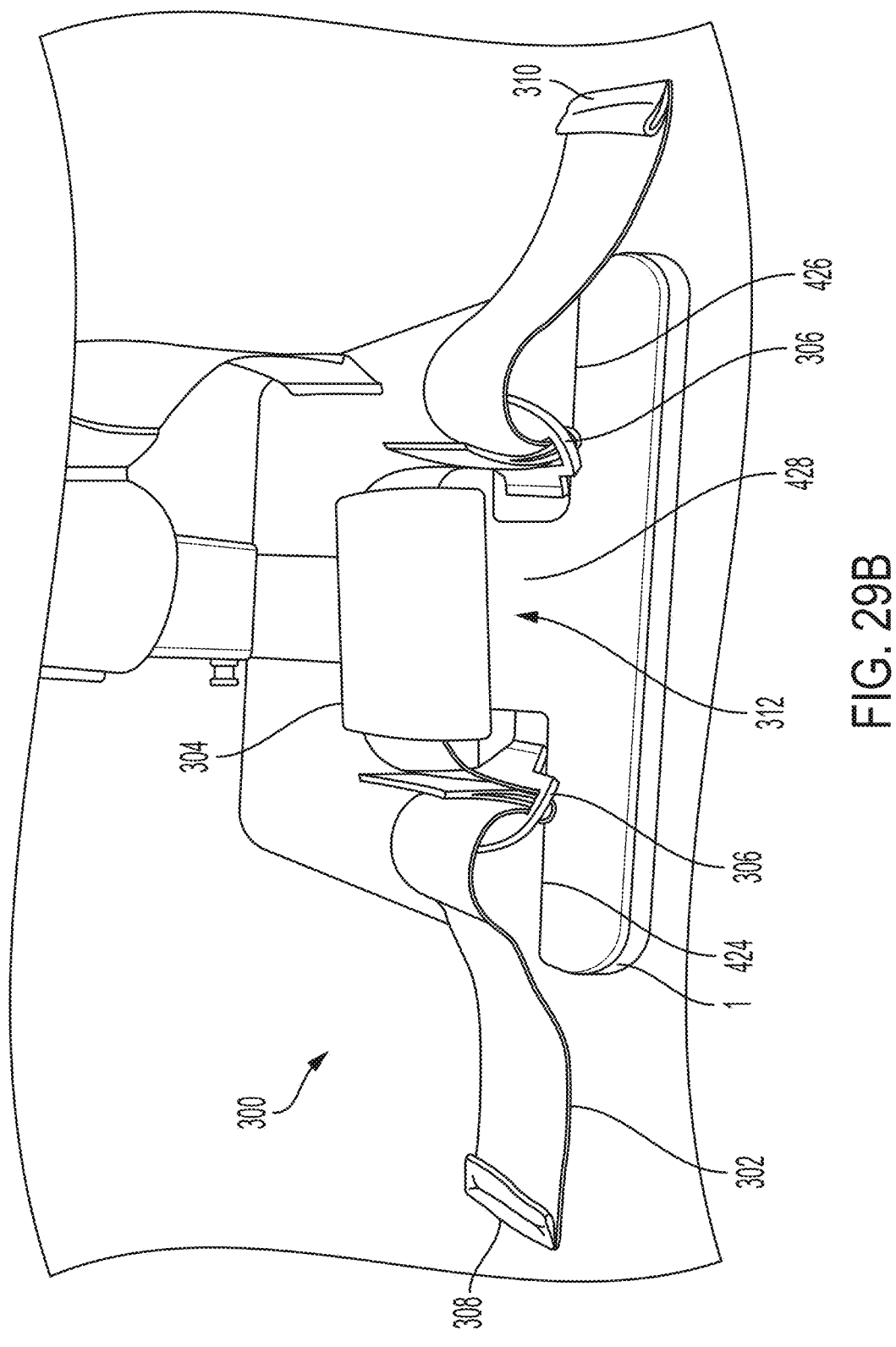
FIG. 29B is a perspective view photographic representation of the strap connected to a base plate of the traction tower, according to an alternative embodiment.

In FIGS. 28A-28B, the length of material 302 is shown woven through the buckles 306 and the buckles 306 are substantially equidistant from the pad 304. Further, as shown in FIGS. 28A-28B, a first end 308 of the length of material 302 extends from a first buckle 306 toward the pad 304 and a second end 310 of the length of material 302 extends from a second buckle 306 toward the pad 304. In use, an opening 312 with a first diameter is created between the base plate 1 of the traction tower 100 and the length of material 302, as shown in FIGS. 29A-29B. To secure the patient's forearm to the traction tower, the patient's arm is inserted through the opening 312. The opening 312 is then reduced to a second diameter by tensioning the first and second ends 308, 310 of the length of material 302 through the buckles 306.

As shown in FIGS. 29A-29B, the first and second buckles 306 slide into slots 424, 426 of the base plate 1 and are able to move towards a center 428 of the base plate 1 to adapt for the patient's arm size. In the depicted embodiment, the slots 424, 426 are on opposing sides of the base plate 1. In FIG. 29A-29B, the slots 424, 426 are aligned such that the central axes of the slots 424, 426 are the same. The benefit of this connection is that the sliding of the buckles 306 within the base plate 1 functions as an additional adjustment mechanism. In particular, when the buckles 306 of the strap 300 are moved closer to the patient's bicep, the length of the strap 300 can be tensioned further, minimizing the opening 312 and making the strap 300 more effective at restricting movement. When the strap 300 is a bicep strap, it is meant to restrict vertical movement of the biceps due to the traction applied to the wrist as well as the side-to-side movements caused when the surgeon applies forces to the wrist during the procedure. The straps 300 in FIGS. 29A-29B are forearm straps, which are very similar to the biceps strap 300 in FIGS. 28A-28B. In an embodiment, forearm straps 300 (FIGS. 29A-29B) comprise a 2-inch-wide webbing to hold the patient's forearm and two plastic buckles 306 which allow it to connect with the upper tower component 3 of the traction tower 100 and adjustment of the length of the strap 300.

One major benefit of this forearm strap 300 shown in FIGS. 29A-29B is that it connects to the upper tower component 3 of the traction tower 100. Since the upper tower 3 of the traction tower 100 can be positioned higher or lower based upon the patient's anatomy, the forearm strap 300 will always be positioned close to the patient's wrist. The closer the strap 300 is to the side forces being applied by the surgeon during the procedure, the more effective it will be at preventing side to side movement of the wrist.

Figure 30A:
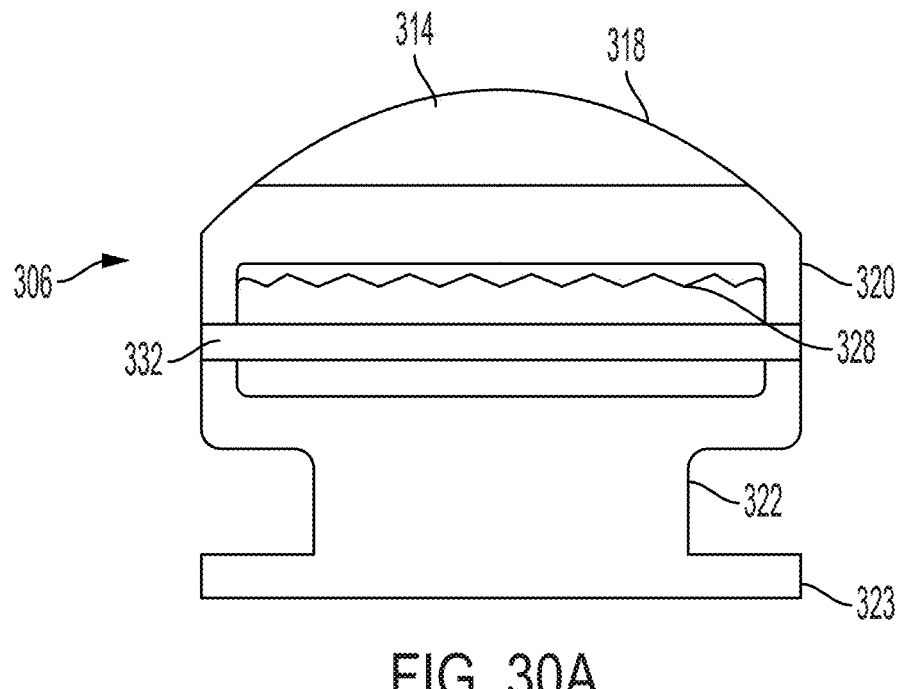
FIG. 30A is a front view schematic representation of a buckle, according to an embodiment.
Figure 30B:
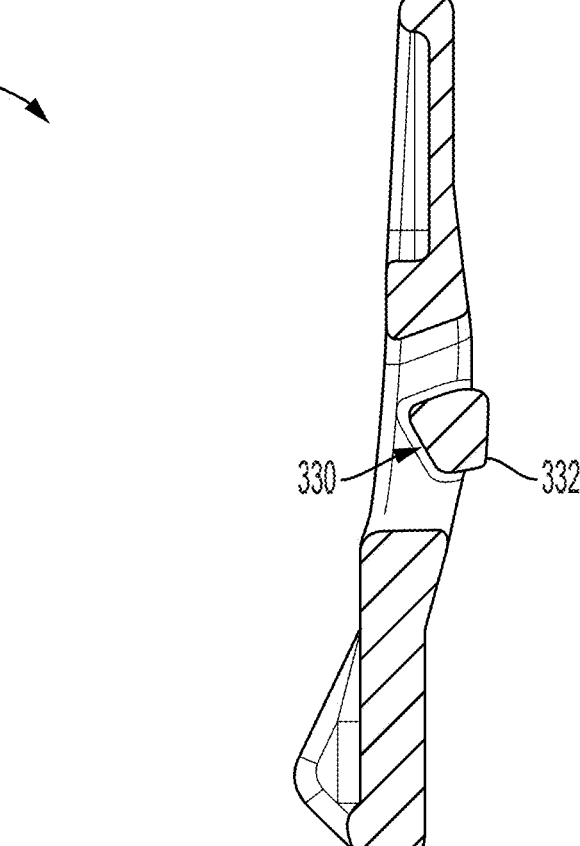
FIG. 30B is a side view schematic representation of a buckle, according to an embodiment.
Figure 30C:
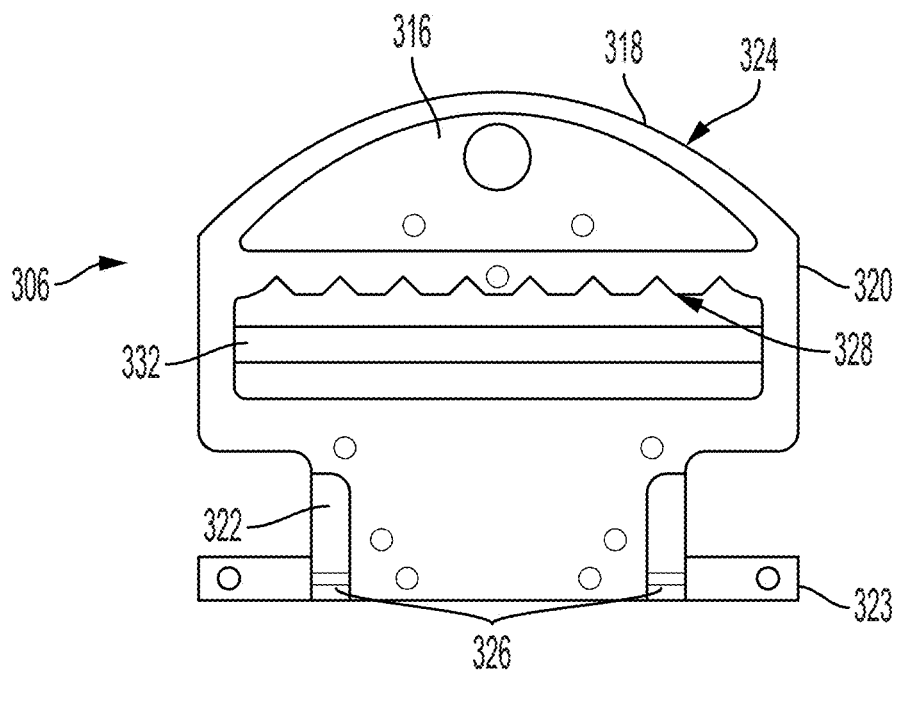
FIG. 30C is a back view schematic representation of a buckle, according to an embodiment.

Referring to FIGS. 30A-30C, there are shown front, side, and back views schematic representations of the buckle 306, according to an embodiment. The buckles 306 shown in FIGS. 30A-30C are easily adjustable and have high locking strength. In the side view shown in FIG. 30B, the buckle 306 has a rounded profile. In other words, the top surface 314 (FIG. 30A) and the bottom surface 316 (FIG. 30C) of the buckle 306 are curved such that the buckle 306 lays comfortably against the patient's arm and adapts well to arms of different sizes.

Referring to FIGS. 30A and 30B, the buckle 306 has a rounded top portion 318 connected to a rectangular adjustability section 320. The adjustability section 320 is connected to a substantially rectangular base portion 322 with one or more connectors 323 extending therefrom. The side view of the buckle 306 shows that the side profile of the buckle 306 is rounded from the top portion 318 to the base portion 322. In FIG. 30C, the bottom surface 316 of the buckle 306 has a ridge 324 extending around the perimeter of the top portion 318. The ridge 324 is designed to function as an ergonomic thumb ridge to allow for an increased grip on the buckle 306 by the user for ease in releasing the strap 300 around the patient's arm. The increased grip is especially beneficial when the user is manipulating the strap 300 with wet gloves.

As shown in FIG. 30C, the bottom surface 316 of the buckle 306 has one or more flanges 326 extending from the base portion 322. In the embodiment shown in FIG. 30C, there are two substantially parallel flanges 326 extending from the base portion 322. The flanges 326 are triangular, as shown in the side profile of the buckle 306 in FIG. 30B. The flanges 326 guide the buckle 306 when the user slides the buckle 306 into the base plate 1 of the traction tower 100. The flanges 326 add rigidity to the base portion 322 where the buckle 306 experiences most of the force.

Referring to FIGS. 30A and 30C, the adjustability section 320 of the buckle 306 includes teeth 328. The teeth 328 extend across the adjustability section 320 to increase strength of the buckle 306 when tightened. The teeth 328 provide increased grip on the length of material 302 and resist slippage when tightened.

Turning back to FIG. 30B, the overall profile of the buckle 306 is thin. This allows the buckle 306 to encompass the bottom of the bicep as well. The buckle 306 has an interference angle extending along an outer edge 330 of the prong 332 extending across the adjustability section 320. The interference angle in the buckle 306 of FIG. 30B is steep, within the range of 0-45 degrees. The steep interference angle provides high friction between the length of material 302 while in use and an easy release when the first or second end 308, 310 of the length of material 302 is pulled down away from the patient's arm.

Figure 31A:
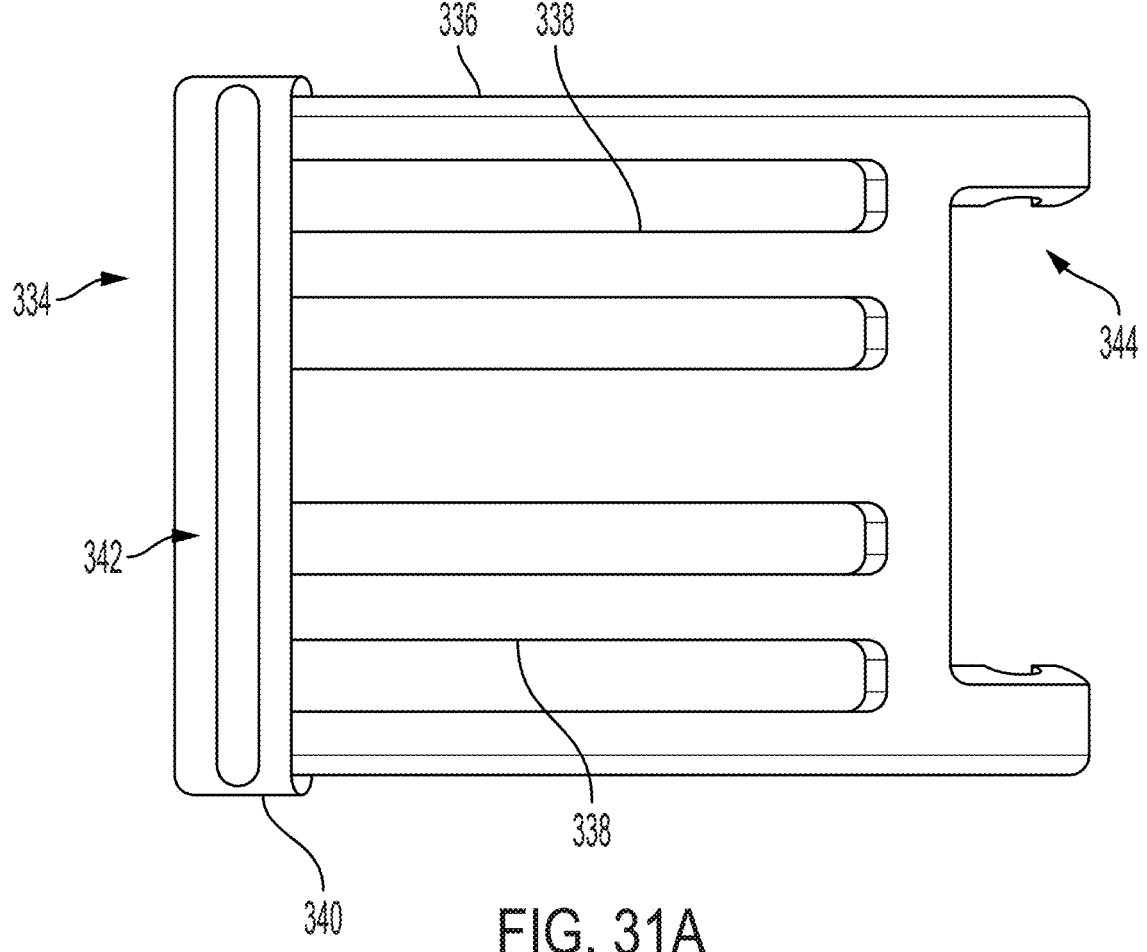
FIG. 31A is a front view schematic representation of a buckle mount, according to an embodiment.
Figure 31B:
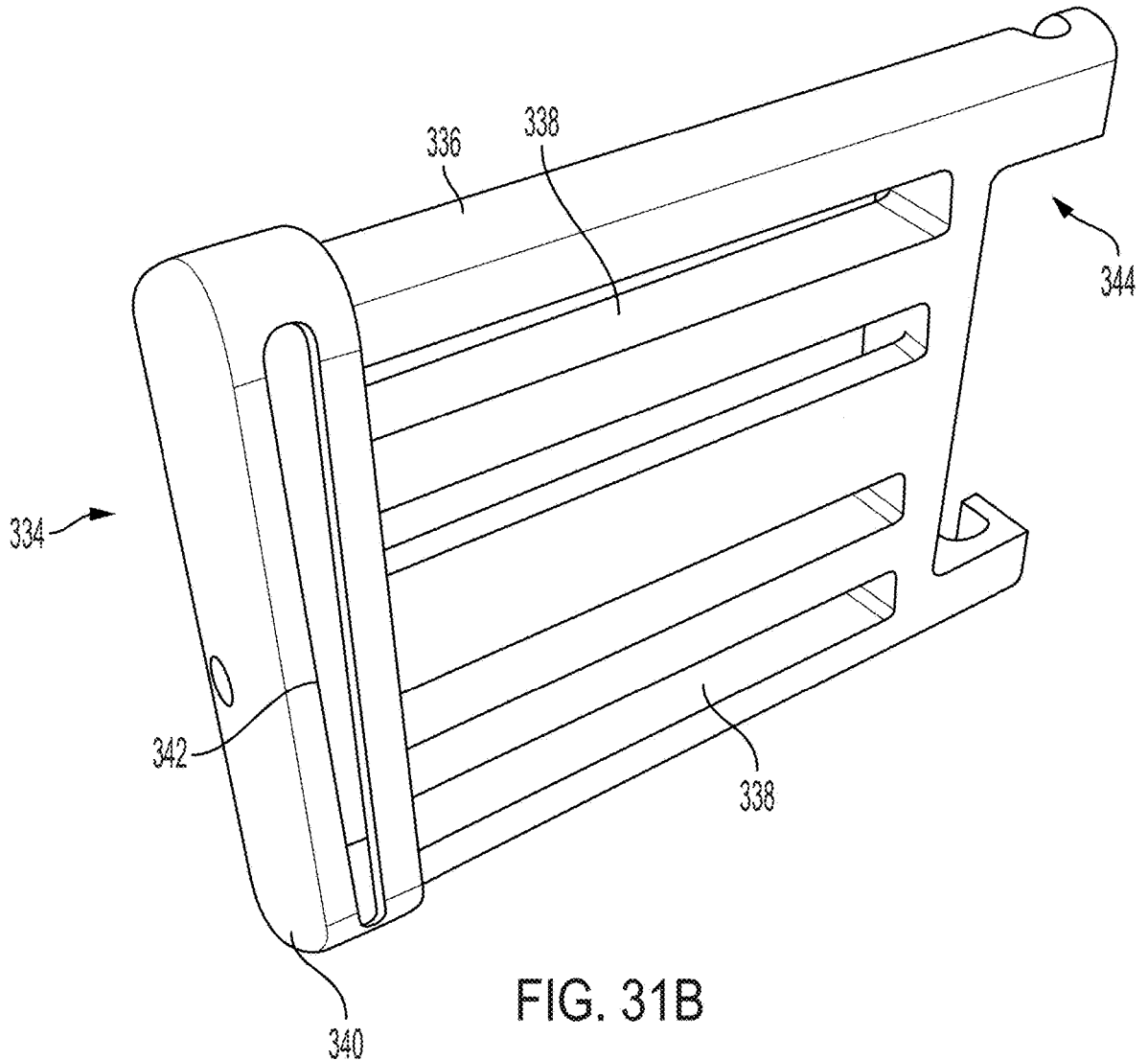
FIG. 31B is a perspective view schematic representation of a buckle mount, according to an embodiment.

Referring now to FIGS. 31A and 31B, there are shown front and perspective views schematic representations of a forearm buckle mount 334, according to an embodiment. The forearm buckle mount 334 attached to the buckle 306 and is used to secure a patient's forearm to the traction tower 100. The forearm buckle mount 334 comprises a rectangular columned section 336 with one or more columns 338 extending thereacross. In the depicted embodiment, the columned section 336 has at least two spaced columns 338 extending thereacross. The forearm buckle mount 334 includes an outer flange 340 connected to the columned section 336. The outer flange 340 includes a slot 342. The slot 342 extends along an axis that is perpendicular to axes extending through each column 338. The slot 342 is asymmetrical to only allow the correct insertion orientation while preventing incorrect insertion orientation. The forearm buckle mount 334 encourages free, low friction rotation of the length of material 302. On a side of the forearm buckle mount 334 opposing the outer flange 340, the forearm buckle mount 334 includes a buckle interface 344 for rotatably attaching to the connectors 323 of the buckle 306.

Figure 32:
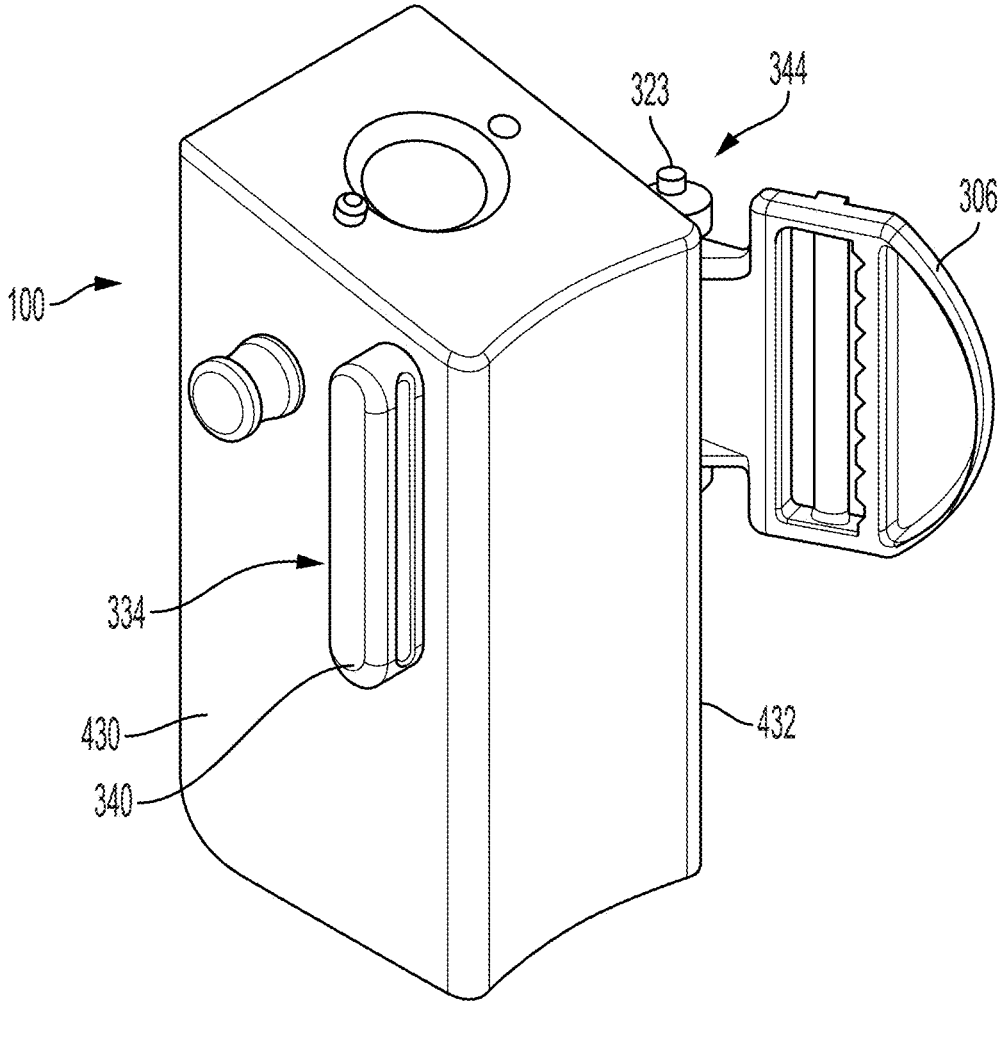
FIG. 32 is a side perspective view schematic representation of a buckle attached to the traction tower, according to an embodiment.
Figure 33:
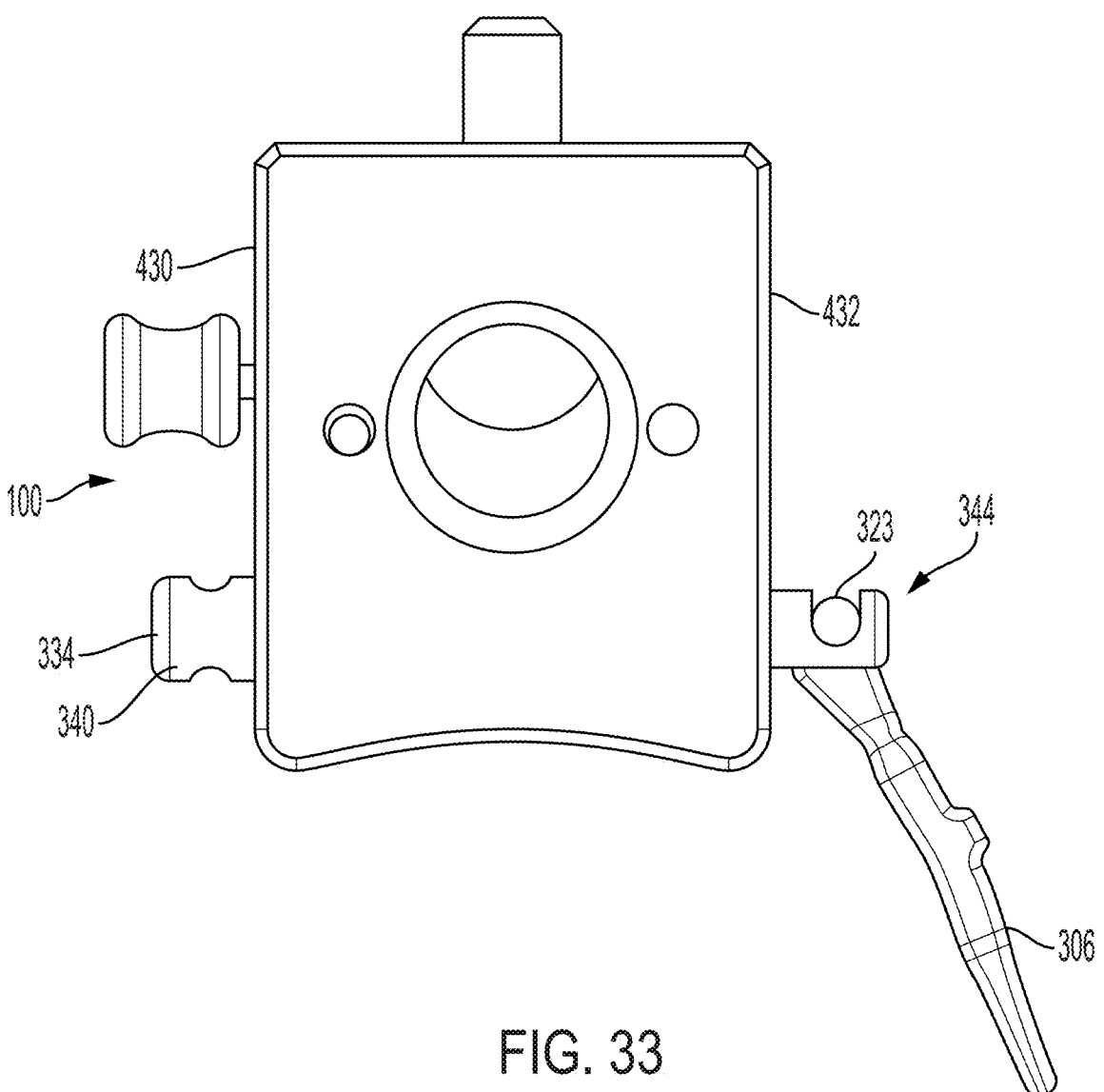
FIG. 33 is a top view schematic representation of a buckle attached to the traction tower, according to an embodiment.
Figure 34:
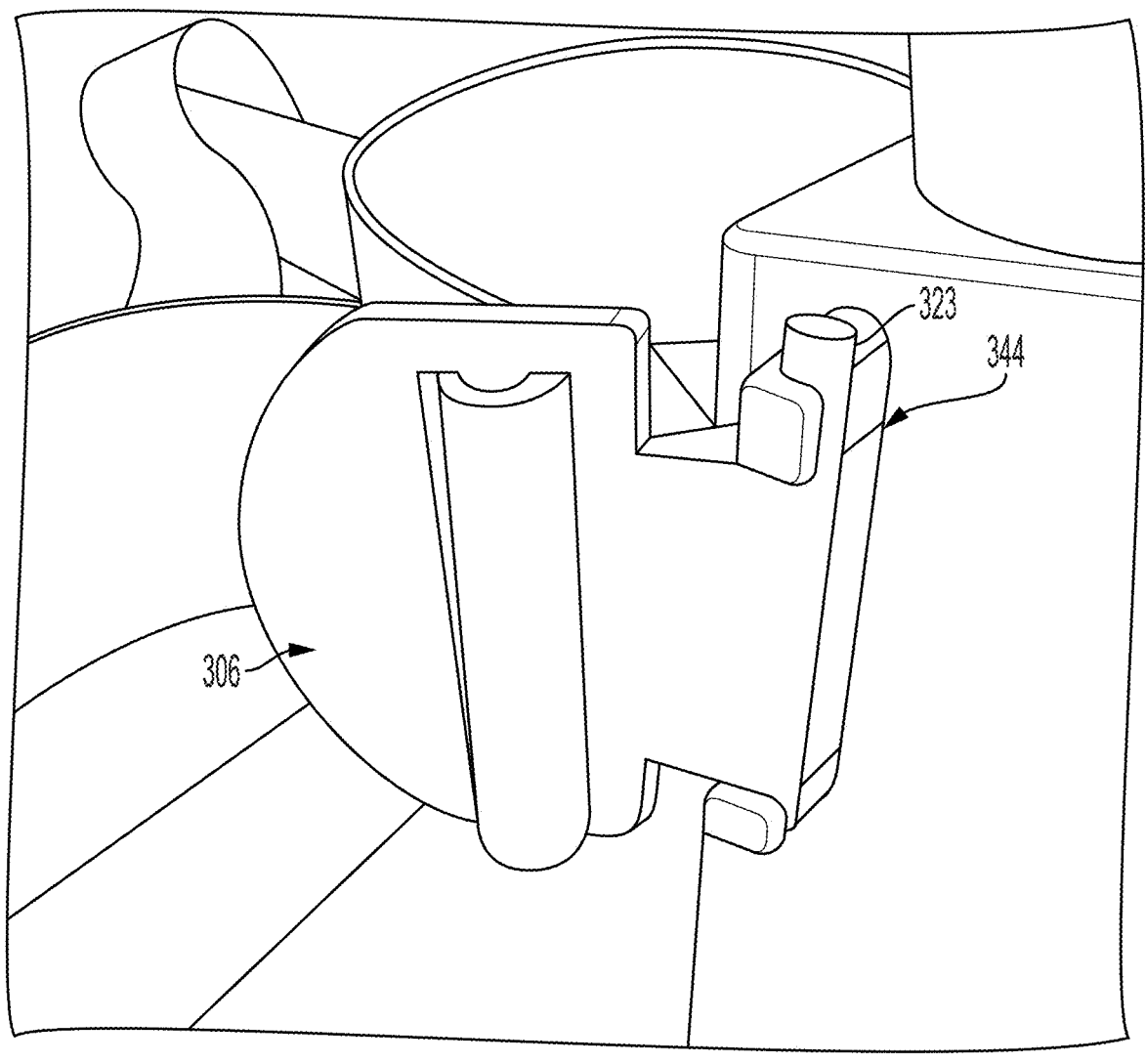
FIG. 34 is a close-up perspective view photographic representation of a buckle attached to the traction tower, according to an embodiment.
Figure 35:
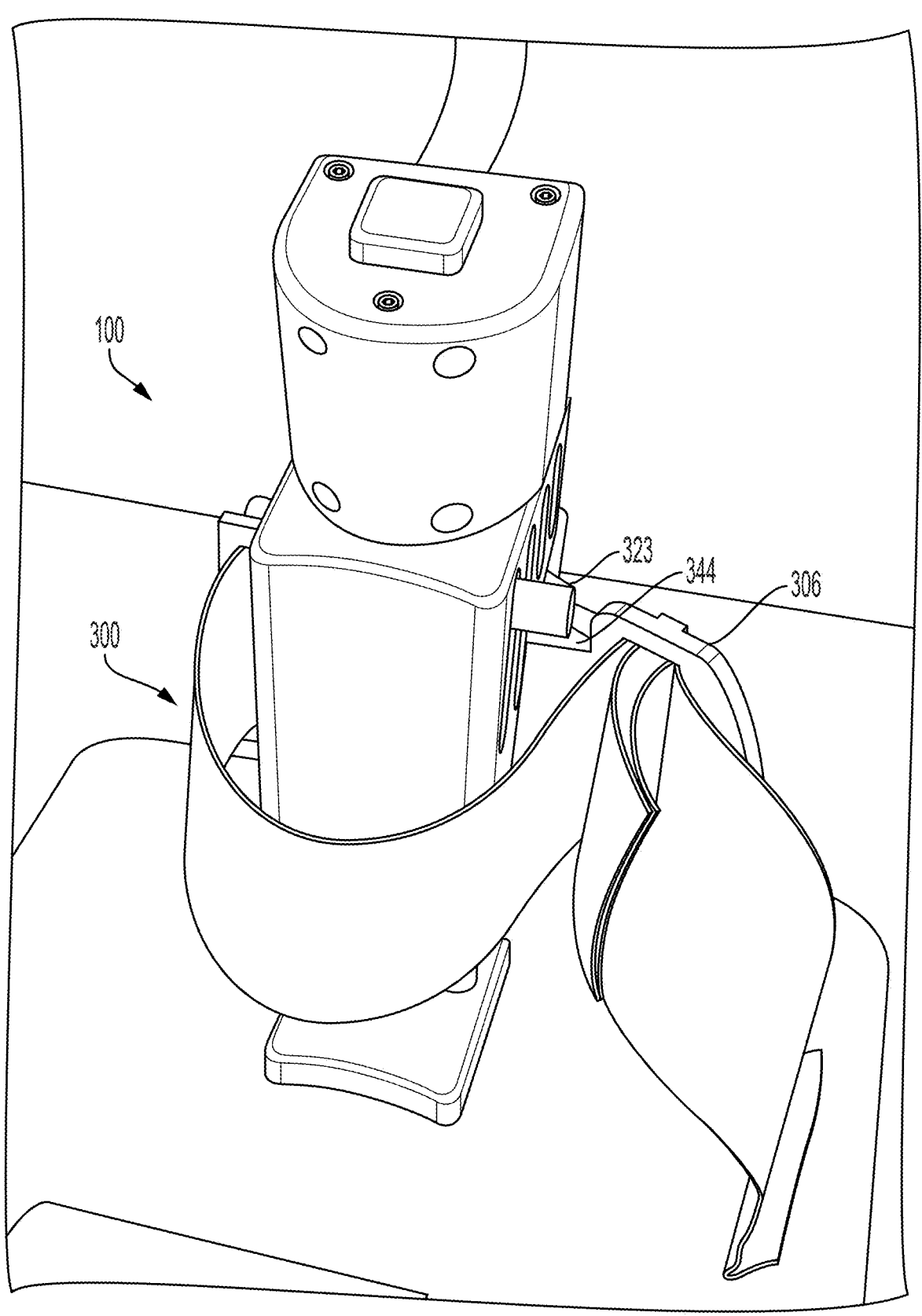
FIG. 35 is a front perspective view photographic representation of a strap attached to a traction tower, according to an embodiment.

Turning to FIGS. 32-34, the buckle 306 and the forearm buckle mount 334 are shown attached to the traction tower 100. As shown in FIG. 32, the outer flange 340 of the forearm buckle mount 334 extends from a first side 430 of the traction tower 100 and the buckle interface 344 of the forearm buckle mount 334 extends from an opposing second side 432 of the traction tower 100. As shown in the top view in FIG. 33, the buckle 306 is rotatable about the buckle interface 344 of the forearm buckle mount 334 relative to the second side 432 of the traction tower 100. The buckle interface 344 has an audible snap and haptic feedback to indicate that the connectors 323 of the buckle 306 have been attached to the forearm buckle mount 334. FIG. 35 shows the traction tower 100 with the strap 300 attached. The buckle 306 stays in place within the buckle interface 344 while in use and easily snaps out when the user is done using the buckle 306. The same buckles 306 are used as the bicep strap 300 with full rotation availability.

Figure 36:
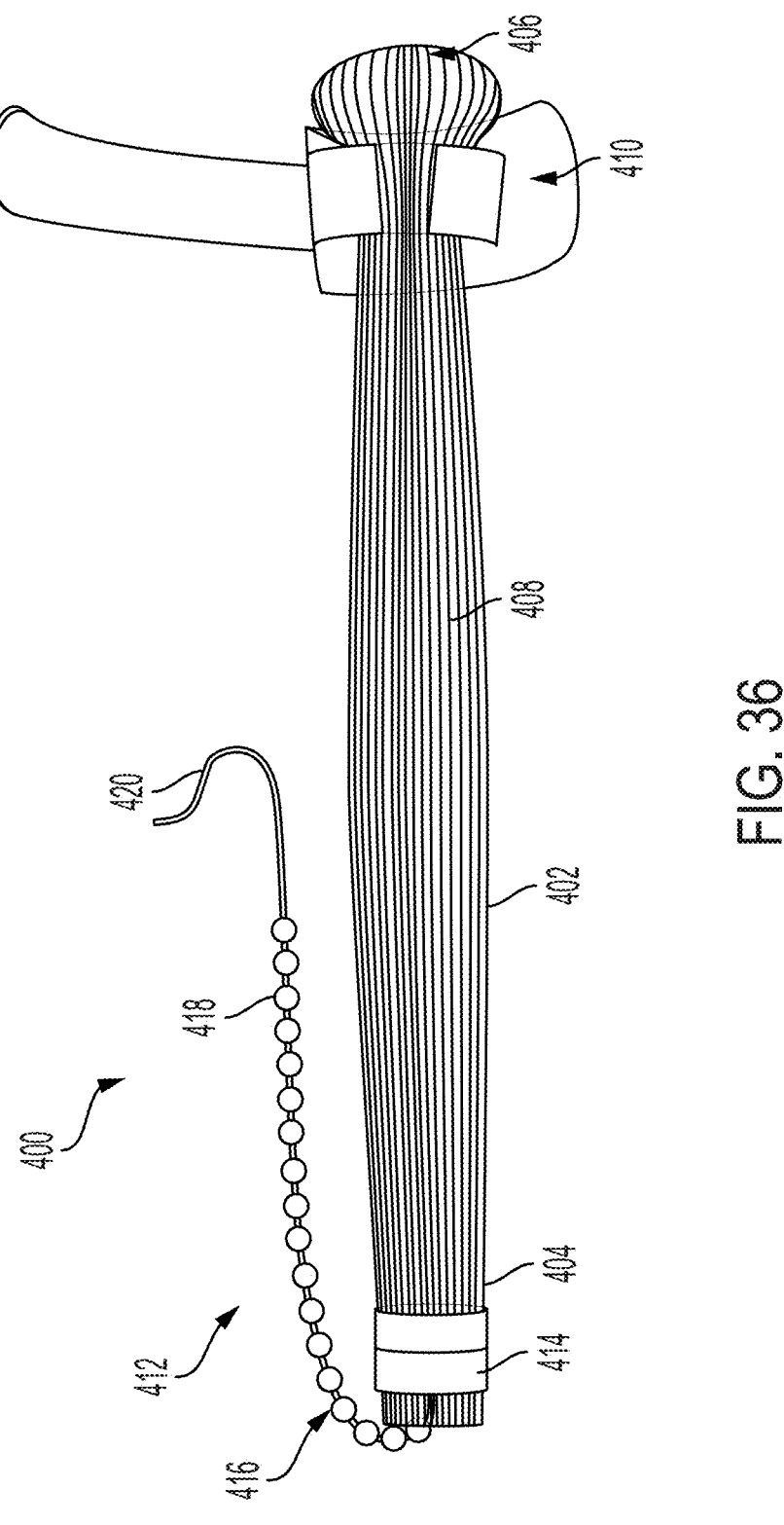
FIG. 36 is a top view schematic representation of a finger trap, according to an embodiment.

Turning now to FIG. 36, there is shown a top view schematic representation of a finger trap 400, according to an embodiment. The finger trap 400 has a length of flexible material 402 with a first end 404 and a second end 406. In an embodiment, the length of flexible material 402 is composed of mesh or braided material. For example, the length of flexible material 402 can be a double-layered mesh material. The length of flexible material 402 is closed at the first end 404 and open at the second end 406. In the depicted embodiment, the length of flexible material 402 is tapered or funneled with a reduced diameter at the first end 404 and an increasing diameter toward the second end 406. The length of flexible material 402 is tubular and rounded with an inner volume 408 for ease of finger insertion. In an embodiment, the length of flexible material 402 is approximately six inches in length to accommodate various sizes of fingers.

Still referring to FIG. 36, a fastener 410 is attached at or near the second end 406 of the finger trap 400. In the depicted embodiment, the fastener 410 is a hook and loop fastener 410. The fastener 410 is woven through the length of flexible material 402 at at least one location. Specifically, as shown in FIG. 36, the fastener 410 extends through the length of flexible material 402 into the inner volume 408 and back out through the length of flexible material 402. The fastener 410 is used to adjust the diameter of the inner volume 408 of the length of flexible material 402 at or near the second end 406. This allows for the quick and easy adjustment of the finger trap 400. With the fastener 410 locked, the fastener 410 resists shear forces from the finger of the patient being pulled out.

As also shown in FIG. 36, the finger trap 400 includes a tension mechanism 412 extending therefrom. The tension mechanism to increase or decrease tension on the finger trap 400. In the depicted embodiment, the tension mechanism 412 is a crimp ball chain. The crimp ball chain comprises a collar 414 extending around the length of flexible material 402 at or near the first end 404. The collar 414 has a ball chain 416 extending therefrom. The ball chain 416 is a chain composed of a series of spaced beads 418. The ball chain 416 terminates in a hook 420 for attachment to the traction tower 100. The traction tower 100 tensions to the hook 420 and the user can increase and decrease tension by replacing the ball chain 416 in the rack 203 at the desired tension.

Figure 37:
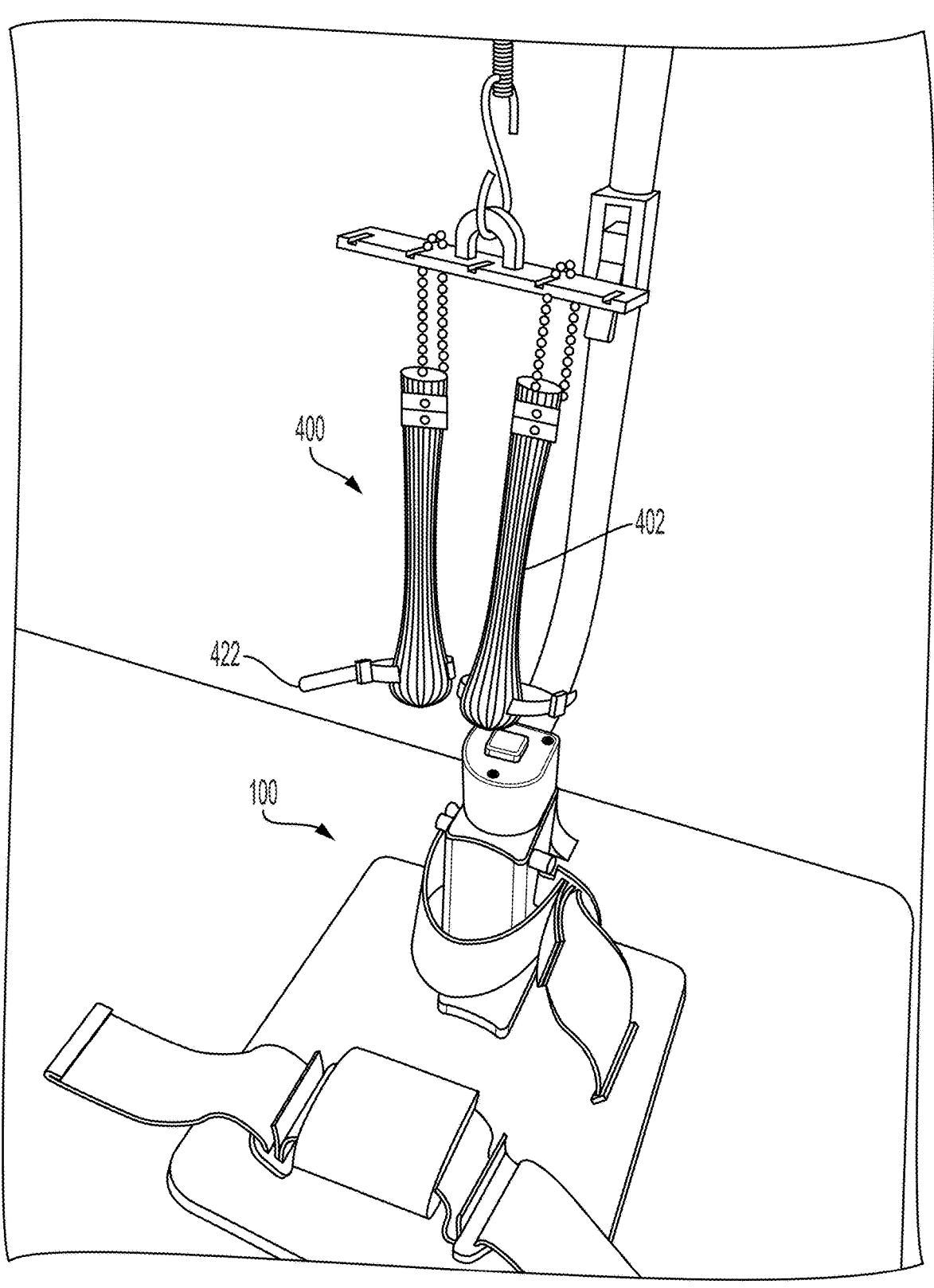
FIG. 37 is a perspective view photographic representation of a finger trap attached a traction tower, according to an embodiment.

Turning now to FIG. 37 there is shown a perspective view photographic representation of a finger trap 400 attached to the traction tower 100, according to an embodiment. In the embodiment shown in FIG. 37, the finger trap 400 feature a releasable cable tie 422 which allows the surgeon to tighten and loosen the finger trap 400 on patients finger. The finger trap 400 incorporated the adjustable cable tie 422 to make these finger trap a one-size fits all. Instead of relying on the length of flexible material 402 to be closely sized to the patient's finger, requiring several different finger trap sizes, the cable tie 422 can be tightened to initiate the length of flexible material 402 holding the finger.

Another advantage of the finger trap 400 shown in FIG. 37 is that the cable tie 422 can be released (non-destructively) if the finger trap 400 needs to be removed and placed onto another finger or the thumb. Traditionally, a finger trap that functions on the patient's index finger or ring finger is not likely to work on the thumb or pinky finger. This could lead to scenarios wherein surgeons will have to use oversized finger traps to ensure they at least fit on all the fingers of the patient. This requires that the surgeons compensate for the large size by taping over of the finger traps on the smaller fingers to try to secure them. Additionally, the surgeon has to adjust the traction settings from the traction tower 100 more frequently because the finger traps would slip (due to oversize), resulting in a loss of traction.

An additional benefit to the configuration of the finger traps 400 shown in FIG. 37 is that the adjustable cable ties 422 never directly contact the patient's fingers. The cable ties 422 only pierce through a single layer of the length of flexible material 402 (e.g., doubled over braided hose). This ensures that the length of flexible material 402 engages with the entire circumference of the finger so that when traction is applied, the length of flexible material 402 performs the function of dispersing the traction force over the entire finger instead of just where the cable tie 422 is tightened.

It should be understood that the values used above are only representative values, and other values may be in keeping with the spirit and intention of this disclosure.

While several inventive embodiments have been described and illustrated herein with reference to certain exemplary embodiments, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein (and it will be understood by one skilled in the art that various changes in detail may be effected therein without departing from the spirit and scope of the invention as defined by claims that can be supported by the written description and drawings). More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Further, where exemplary embodiments are described with reference to a certain number of elements it will be understood that the exemplary embodiments can be practiced utilizing either less than or more than the certain number of elements.

All references, including publications, patent applications, and patents, cited herein are hereby incorporated by reference to the same extent as if each reference were individually and specifically indicated to be incorporated by reference and were set forth in its entirety herein.

All definitions, as defined and used herein, should be understood to control over dictionary definitions, definitions in documents incorporated by reference, and/or ordinary meanings of the defined terms.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if not directly attached to where there is something intervening.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A traction tower assembly, comprising:
   a tower assembly comprising a tower connected to a base plate with a first slot and a second slot extending partially therethrough, a central longitudinal axis of the first slot being co-linear with a central longitudinal axis of the second slot, wherein:
   each of the first slot and the second slot extends from a first open end to a second closed end opposite the first end,
   the second end of the first slot is a portion of the first slot that is closest to the second end of the second slot; and
   a strap comprising a length of material attached to a first adjustment mechanism having a central longitudinal axis and a second adjustment mechanism having a central longitudinal axis; and
   wherein the first adjustment mechanism is slidable within the first slot of the base plate between the first end to a terminal position at the second end of the first slot, and the second adjustment mechanism is slidable within the second slot of the base plate between the first end to a terminal position at the second end of the second slot;
   wherein when the first and second adjustment mechanisms are moved from the first end to the terminal position at the second end of the respective slots, the central longitudinal axes of the first and second adjustment mechanisms remain substantially parallel with the central longitudinal axes of the respective slots; and
   wherein the strap and the first and second adjustment mechanisms are capable of restricting vertical and side-to-side movements of a user in traction.

2. The assembly of claim 1, wherein when the first and second adjustment mechanisms are within the first and second slots of the base plate, the strap forms an opening having a first diameter with the base plate.

3. The assembly of claim 2, wherein the length of material comprises a free first end and a free second end, and tensioning the free first end or free second end reduces the opening to a diameter.

4. The assembly of claim 1, further comprising a pad attached to at least a portion of the length of material.

5. The assembly of claim 4, wherein the pad is tubular, extending around the at least a portion of the length of material.

6. The assembly of claim 1, wherein the adjustment mechanism is a buckle.

* * * * *